(12) United States Patent
Schwögler et al.

(10) Patent No.: US 7,820,647 B2
(45) Date of Patent: Oct. 26, 2010

(54) 2-SUBSTITUTED PYRIMIDINES AND THEIR USE AS PESTICIDES

(75) Inventors: Anja Schwögler, Mannheim (DE);
Frank Schieweck, Heβheim (DE);
Joachim Rheinheimer, Ludwigshafen (DE); Markus Gewehr, Kastellaun (DE); Bernd Müller, Frankenthal (DE); Thomas Grote, Wachenheim (DE); Wassilios Grammenos, Ludwigshafen (DE); Udo Hünger, Mainz (DE); Carsten Blettner, Mannheim (DE); Peter Schäfer, Ottersheim (DE); Oliver Wagner, Neustadt (DE); Reinhard Stierl, Freinsheim (DE); Ulrich Schöfl, Brühl (DE); Siegfried Strathmann, Limburgerhof (DE); Maria Scherer, Godramstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 805 days.

(21) Appl. No.: 11/596,891

(22) PCT Filed: May 17, 2005

(86) PCT No.: PCT/EP2005/005333

§ 371 (c)(1),
(2), (4) Date: Nov. 17, 2006

(87) PCT Pub. No.: WO2005/113538

PCT Pub. Date: Dec. 1, 2005

(65) Prior Publication Data

US 2008/0176831 A1    Jul. 24, 2008

(30) Foreign Application Priority Data

May 19, 2004    (DE) .................... 10 2004 025 363

(51) Int. Cl.
*C07D 239/48*    (2006.01)
*C07D 403/04*    (2006.01)
*A01N 43/54*    (2006.01)
*A01N 43/58*    (2006.01)
*A01N 43/34*    (2006.01)
*A01P 3/00*    (2006.01)

(52) U.S. Cl. .................... 514/212.08; 514/252.02; 514/275; 544/325; 544/238; 540/524

(58) Field of Classification Search ............. 514/273, 514/275, 212.08, 252.02; 544/321, 326, 544/238, 325; 540/524
See application file for complete search history.

(56) References Cited

U.S. PATENT DOCUMENTS 7,470,700 B2 *   12/2008   Feng et al. .................... 514/272
2001/0011094 A1 *   8/2001   Andries et al. .................... 514/269
2004/0116429 A1    6/2004   Grote et al.
2006/0148764 A1    7/2006   Gypser
2006/0194783 A1 *   8/2006   Burgey et al. .................... 514/211.03
2008/0176744 A1 *   7/2008   Schwogler et al. .................... 504/100
2008/0269235 A1 *   10/2008   Dal Piaz et al. .................... 514/252.03

FOREIGN PATENT DOCUMENTS

| DE | 1 056 279 | 4/1959 |
|---|---|---|
| EP | 0 715 851 A2 | 6/1996 |
| WO | WO-99/41255 A1 | 8/1999 |
| WO | WO-02/07473 A1 | 1/2002 |
| WO | WO-02/074753 A | 9/2002 |
| WO | WO-03/043993 A | 5/2003 |
| WO | WO-2004/103978 A | 12/2004 |

OTHER PUBLICATIONS

Booth et. al., Tetrahedron Letters, vol. 33, No. 3, pp. 413-416 (1992).
Miyachi et. al., Tetrahedron Letters, vol. 34, No. 51., pp. 8267-8270 (1993).
Casson et. al., Journal Chemical Society Perkin Trans., vol. 1 (1994).
Evans et. al., Aust. J. Chem vol. 43, pp. 733-740 (1990).
Sato et. al., J. Chemical. Soc., Perkin Trans., vol. 1 (1996).
King et. al., J. Org. Chem. vol. 43, No. 2, pp. 358-360 (1978).
Miyaura et. al., J.C.S. Chem. Comm., pp. 866-867 (1979).
Derwent English Abstract 2005-021189.

* cited by examiner

*Primary Examiner*—James O Wilson
*Assistant Examiner*—Cecilia M Jaisle
(74) *Attorney, Agent, or Firm*—Birch, Stewart, Kolasch & Birch, LLP

(57) ABSTRACT

The invention relates to 2-substituted pyrimidines of the formula I in which the index n and the substituents L and $R^1$ to $R^3$ are as defined in the description and
X is a group —CH—$R^a$—, —N—$R^b$—, —O— or —S—;
  $R^a$ may be hydrogen, halogen, $C_1$-$C_6$-alkyl, $C_1$-$C_6$-alkoxy, cyano or $C_1$-$C_6$-alkoxycarbonyl;
  $R^b$ is hydrogen, $C_1$-$C_6$-alkyl or $C_3$-$C_6$-cycloalkyl;
T is a group —CH—$R^a$—;
p is an integer from 1 to 4;
Y is a group —CH—$R^a$— or —N—$R^b$—,
  o is 0 or 1;
Z is O, S or a group N($R^c$)
  $R^c$ is hydrogen, $C_1$-$C_6$-alkyl or $C_1$-$C_6$-alkoxy,
and to processes for their preparation, to pesticidal compositions comprising them and to their use as pesticides.

9 Claims, No Drawings

2-SUBSTITUTED PYRIMIDINES AND THEIR USE AS PESTICIDES

The invention relates to 2-substituted pyrimidines of the formula I

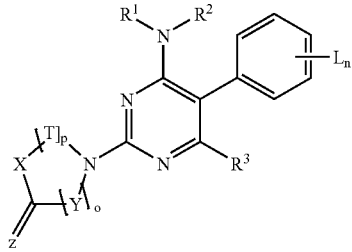

in which the indices and the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, —C(=O)—N(A')A, C(A')(=N—OA), N(A')A, N(A')-C(=O)-A, N(A'')—C(=O)—N(A')A, S(=O)$_m$-A, S(=O)$_m$—O-A or S(=O)$_m$—N(A')A, m is 0, 1 or 2;

A, A', A'' independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which comprises one to four heteroatoms from the group consisting of O, N and S;

where the aliphatic groups of the radical definitions of L for their part may be partially or fully halogenated or may carry one to four groups $R^u$:

$R^u$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy —C(=O)-A, —C(=O)—O-A, —C(=O)—N(A')A, C(A')(=N—OA), N(A')A, N(A')-C(=O)-A, N(A'')—C(=O)—N(A')A, S(=O)$_m$-A, S(=O)$_m$—O-A or S(=O)$_m$—N(A')A;

$R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A'')—C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether -(—O—), carbonyl —(C=O)—, thio -(—S—), sulfoxyl -(—S[=O]—) or sulfenyl -(—SO$_2$—) group or by a further amino -(—N($R^a$)— group, where $R^a$ is hydrogen or $C_1$-$C_6$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

X is a group —CH—$R^a$, —N—$R^b$—, —O— or —S—;

$R^a$ may be hydrogen, halogen, $C_1$-$C_6$-alkyl, $C_1$-$C_6$-alkoxy, cyano or $C_1$-$C_6$-alkoxycarbonyl;

$R^b$ is hydrogen, $C_1$-$C_6$-alkyl or $C_3$-$C_6$-cycloalkyl;

T is a group —CH—$R^a$—;

p is an integer from 1 to 4;

Y is a group —CH—$R^a$— or —N—$R^b$—, o is 0 or 1;

Z is O, S or a group N($R^c$)

$R^c$ is hydrogen, $C_1$-$C_6$-alkyl or $C_1$-$C_6$-alkoxy.

Moreover, the invention relates to a process for preparing these compounds, to compositions comprising 2-pyrimidines and to their use for controlling phytopathogenic harmful fungi.

Fungicidal pyrimidines carrying a heteroaryl radical in the 2-position are known from WO-A 02/074753. Furthermore, pharmacologically active pyrimidines carrying a 4-methylpiperazine radical in the 2-position are known from EP-A 715 851. EP-A 715 851 does not disclose any fungicidal action.

In many cases, the activity of the pyrimidines which are heteroaryl-substituted in the 2-position is unsatisfactory. Accordingly, it was an object of the present invention to provide compounds having improved activity.

We have found that this object is achieved by the pyrimidines of the formula I defined at the outset. Moreover, we have found processes for their preparation and compositions comprising them for controlling harmful fungi.

The compounds I can be obtained by different routes.

1. It is possible, for example, to use the sulfones of the formula II, whose preparation is described in detail in WO-A 02/074753 or DE 10156279.9, as starting materials. Reaction of the sulfones II with nucleophiles of the formula III where the index p is preferably 2 to 5 gives the lactams IA according to the invention. The reaction is generally carried out under base catalysis. If, in the first step, the nucleophiles III are to be deprotonated, strong bases are generally employed. Suitable bases are, for example, organometallic compounds such as: lithium diisopropylamide, butyllithium or sodium hydride.

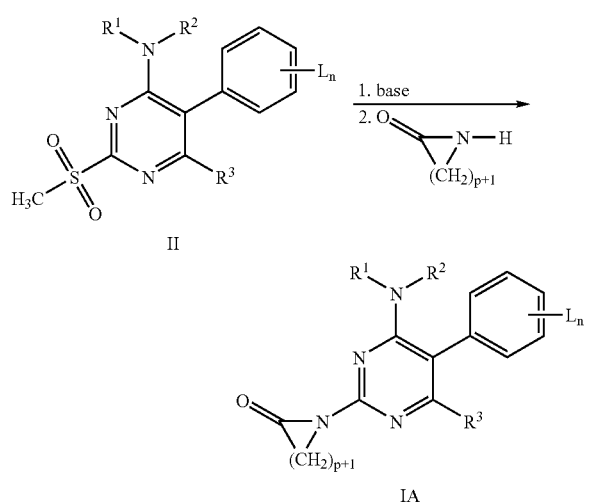

2. Lactam derivatives of the formulae IA' and IA" (Z=S or NR$^C$) can be synthesized from the lactams of the formula IA (Z=O) as shown in the scheme below.

Suitable sulfurizing agents are, for example, Lawesson's reagent or phosphorus pentasulfide. The sulfurization reaction is preferably carried out in an inert diluent, such as, for example, an aliphatic or aromatic hydrocarbon, dimethylformamide or N-methylpyrrolidone. The amination of the thiolactam IA' to the compound IA" is preferably carried out by adding an excess of amine NH$_2$R$^c$. In the case of low-boiling amines, the reaction can preferably be carried out under pressure, for example in an autoclave. In certain cases, it is advisable to add a diluent for the amination, too. Suitable diluents are the compounds that have already been described for the sulfurization. It is also possible to convert the compound IA directly into the compound IA" using methods known from the literature (acid/base catalyzed).

3. Compounds of the formula IB can be obtained, for example, by reacting the hydrazine IV with a chloroalkylcarbonyl chloride, where the index p is 2 or 3, to give the compound V, followed by cyclization to give the pyrazolidinone IB.

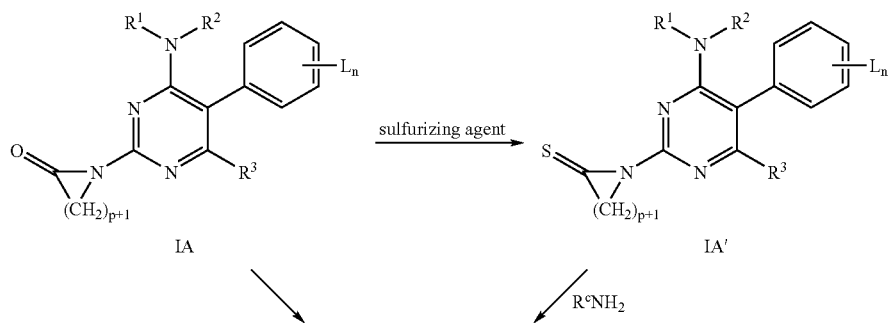

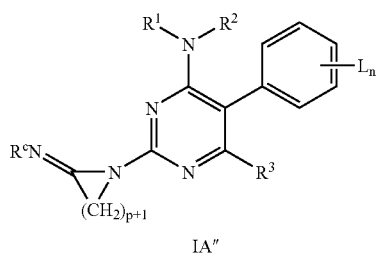

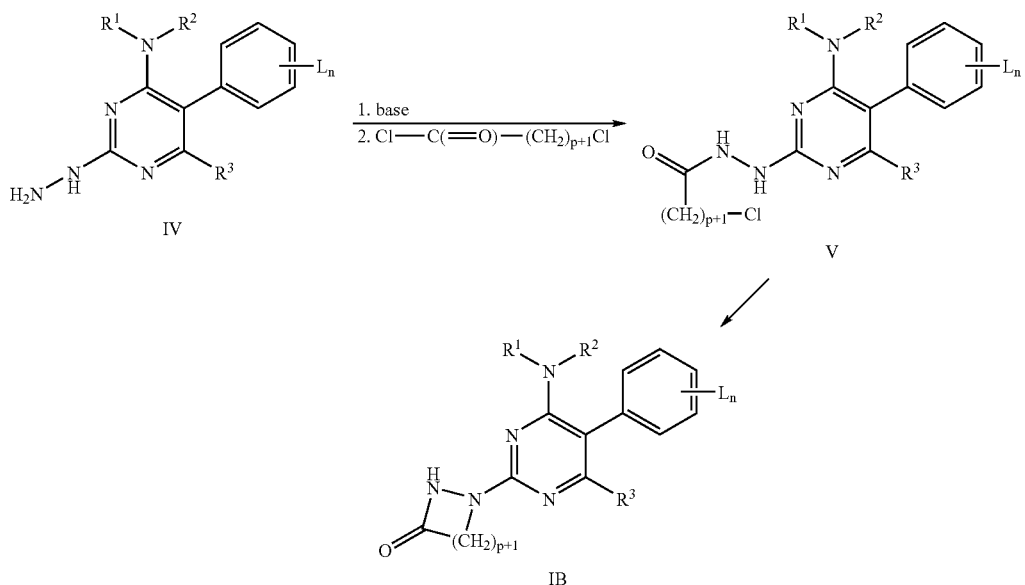

The hydrazine compound IV can be obtained, for example, from the sulfone II by reaction with hydrazine hydrate (see, for example, WO-A 03/043993). The further reaction with a chloroalkylcarbonyl chloride is generally carried out in an inert diluent, such as an optionally halogenated aliphatic or aromatic hydrocarbon or an ether. Preferred bases are pyridine derivatives or tertiary amines. Cyclization to give the pyrazolidinones IB can be carried out, for example, in the presence of organometallic bases, such as butyllithium or LDA. Suitable for this reaction are the customary solvents, such as aliphatic or cyclic ethers.

4. Analogously to the methods described under item 2 and starting with the pyrazolidinones IB, it is possible to obtain the corresponding thio derivatives IB' and imino derivatives IB".

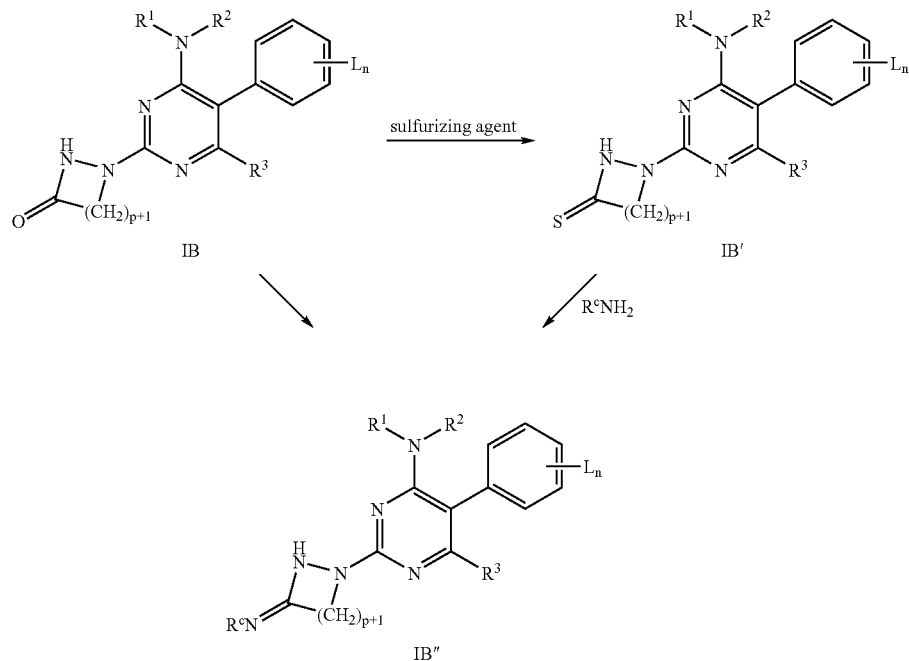

5) Sulfones of the formula II in which $R^3$ has a meaning different from halogen can be obtained as follows:

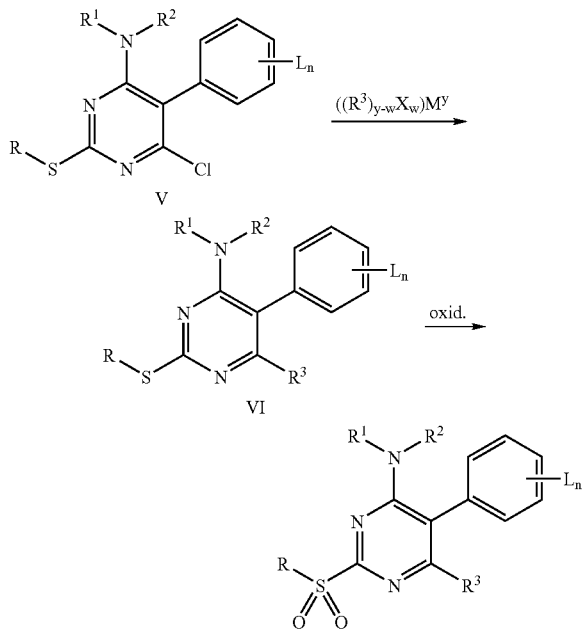

In formula $(R^3)_{y-w}X_w$-$M^y$, M is a metal ion of valency Y, such as, for example, B, Zn, Mg, Cu or Sn, X is chlorine, bromine, iodine or hydroxyl, $R^3$ is preferably $C_1$-$C_4$-alkyl and w is a number from 0 to 3. This reaction can be carried out, for example, analogously to the following methods: J. Chem. Soc. Perkin Trans. 1 (1994), 1187, ibid. 1 (1996), 2345; WO-A 99/41255; Aust. J. Chem., 43 (1990), 733; J. Org. Chem., 43 (1978), 358; J. Chem. Soc. Chem. Commun. (1979) 866; Tetrahedron Lett., 34 (1993), 8267; ibid., 33 (1992), 413.

What was said above applies in particular to the preparation of compounds in which $R^3$ is an alkyl group. If $R^3$ is a cyano group or an alkoxy substituent, the radical $R^3$ may be introduced by reaction with alkali metal cyanides or alkali metal alkoxides.

In the definitions of the symbols given in the formulae above, collective terms were used which are generally representative for the following substituents:

halogen: fluorine, chlorine, bromine and iodine;

alkyl and the alkyl moieties of, for example, alkoxy, alkylamino, alkoxycarbonyl: saturated straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4, 6 or 8 carbon atoms (as mentioned above), where in these groups some or all of the hydrogen atoms may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 4, 6 or 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkadienyl: unsaturated straight-chain or branched hydrocarbon radicals having 4 to 8 carbon atoms and two double bonds in any position;

haloalkenyl: unsaturated straight-chain or branched hydrocarbon radicals having 2 to 8 carbon atoms and a double bond in any position (as mentioned above), where in these groups some or all of the hydrogen atoms may be replaced by halogen atoms as mentioned above, in particular by fluorine, chlorine and bromine;

alkynyl: straight-chain or branched hydrocarbon groups having 2 to 8 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 carbon ring members, for example $C_3$-$C_6$-cycloalkyl such as cyclopropyl, cyclobutyl, cyclopentyl, cyclohexyl;

five- or six-membered saturated, partially unsaturated or aromatic heterocycle which comprises one to four heteroatoms from the group consisting of O, N and S: for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydropyridazinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

ring system which is if appropriate formed by $R^1$ and $R^2$ or by A and A' together with the nitrogen to which they are attached: for example pyrrolidine, morpholine, piperidine or tetrahydropyrazole.

The scope of the present invention includes the (R) and (S) isomers and the racemates of compounds of the formula I having chiral centers.

Hereinbelow, the embodiments of the invention are described in more detail.

With a view to the intended use of the pyrimidines of the formula I, particular preference is given to the following meanings of the substituents, in each case on their own or in combination:

Preference is given to compounds I in which $R^1$ is $C_1$-$C_6$-alkyl, $C_1$-$C_6$-haloalkyl, $C_2$-$C_6$-alkenyl, $C_2$-$C_6$-alkynyl or $C_3$-$C_6$-cycloalkyl and $R^2$ is hydrogen.

Especially preferred are compounds I in which $R^1$ is $C_1$-$C_6$-haloalkyl, $C_2$-$C_6$-alkenyl or $C_1$-$C_6$-alkyl branched in the α-position. Particular preference is given to the compounds I in which $R^1$ is as defined above and $R^2$ is hydrogen.

In addition, preference is given to compounds I in which $R^1$ is $C_1$-$C_4$-haloalkyl and $R^2$ is hydrogen.

Moreover, preference is given to compounds I in which $R^1$ and $R^2$ together with the nitrogen to which they are attached form a five- or six-membered ring which may be interrupted by an oxygen atom and may carry one or two $C_1$-$C_6$-alkyl substituents.

Especially preferred are groups $NR^1R^2$ such as pyrrolidines or piperidines which are methylated—in particular in the α-position. Preference is furthermore given to 4-methylpiperidine.

Especially preferred are pyrimidines I where the substituents $L^1$ to $L^5$ are as defined below:

L is halogen, cyano, methyl, methoxy, —C(=O)—O-A, —C(=O)—N(A')A, C(A')(=N—OA), N(A')A, N(A')-C(=O)-A, A,A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A' together with the atoms to which they are attached are a five- or six-membered saturated heterocycle which comprises one or two heteroatoms from the group consisting of O, N and S.

Moreover, preference is given to pyrimidines I in which the phenyl group substituted by $L_n$ is the group B

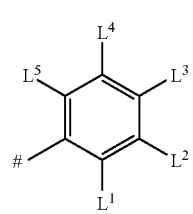

B in which # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, cyano, $CH_3$, $SCH_3$, $OCH_3$, $SO_2CH_3$, CO—$NH_2$, —CO—$NHCH_3$, CO—$NHC_2H_5$, CO—$N(CH_3)_2$, NH—C(=O)$CH_3$, $N(CH_3)$—C(=O)$CH_3$ or COOCH$_3$ and $L^5$ is hydrogen, fluorine, chlorine or $CH_3$.

Particularly preferred are also compounds I in which $R^3$ is $C_1$-$C_4$-alkyl which may be substituted by halogen.

Moreover, particular preference is given to compounds I in which $R^3$ is halogen, cyano, $C_1$-$C_4$-alkyl or $C_1$-$C_4$-alkoxy.

Especially preferred are compounds I in which $R^3$ is methyl, cyano, methoxy or, in particular, chlorine.

Particularly preferred are pyrimidines of the formula I in which the substituent in the 2-position —N-$T_p$-X—C(=Z)—$Y_o$— is a lactam ring.

T is a group —CH—$R^a$—, $R^a$ is hydrogen, halogen, cyano or $C_1$-$C_3$-alkyl, particularly preferably hydrogen p is a number from 1 or 4;

X is a group —CH—$R^a$—, —N—$R^b$—, —O— or —S—; particularly preferably —CH—$R^a$—, $R^a$ is hydrogen or $C_1$-$C_3$-alkyl;

o is 0;

Z is O, S or NR$^C$, preferably O, S, NH, NCH$_3$ or NOCH$_3$ and particularly preferably O or S.

Preference is furthermore given to pyrimidines of the formula I in which the substituent in the 2-position —N-T$_p$-X—C(=Z)—Y$_o$— is as defined below:

T is a group —CH—R$^a$—,
R$^a$ is hydrogen, halogen, cyano or C$_1$-C$_3$-alkyl, particularly preferably hydrogen
p is a number from 1 or 4;
X is a group —CH—R$^a$—, —N—R$^b$—, —O— or —S—; particularly preferably —CH—R$^a$—,
R$^a$ is hydrogen or C$_1$-C$_3$-alkyl;
Y is a group —N—R$^b$—,
R$^b$ is hydrogen or C$_1$-C$_3$-alkyl;
o is 1 and
Z is O, S or NR$^C$, preferably O or S, NH, NCH$_3$ or NOCH$_3$ and particularly preferably O or S.

Preference is furthermore given to 2-substituted pyrimidines of the formula I where n is an integer from 1 to 3, where at least one substituent L is located in the ortho-position on the phenyl ring;
L is halogen, cyano, methyl, methoxy, —C(=O)—O-A, —C(=O)—N(A')A, C(A')(=N—OA), N(A')A, N(A')-C(=O)-A,
A,A' independently of one another are hydrogen, C$_1$-C$_6$-alkyl, C$_2$-C$_6$-alkenyl, C$_2$-C$_6$-alkynyl, phenyl, where the organic radicals may be partially or fully halogenated or may be substituted by C$_1$-C$_4$-alkoxy; or A and A' together with the atoms to which they are attached are a five- or six-membered saturated heterocycle which comprises one or two heteroatoms from the group consisting of O, N and S;
where the aliphatic groups of the radical definitions of L for their part may be partially or fully halogenated;
R$^1$,R$^2$ independently of one another are C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl or C$_2$-C$_6$-haloalkynyl;
R$^2$ may additionally be hydrogen;
R$^1$ and R$^2$ may also, together with the nitrogen atom to which they are attached, form a saturated or unsaturated five- or six-membered ring which may be interrupted by an ether -(—O—) or by a further amino -(—N(R$^a$)— group, where R$^a$ is hydrogen or C$_1$-C$_6$-alkyl, and/or may comprise one or more substituents from the group consisting of halogen, C$_1$-C$_6$-alkyl, C$_1$-C$_6$-haloalkyl and oxy-C$_1$-C$_3$-alkyleneoxy;
R$^3$ is halogen, cyano, C$_1$-C$_4$-alkyl, C$_1$-C$_4$-alkoxy or C$_1$-C$_4$-haloalkyl;
T is a group —CH—R$^a$—,
R$^a$ is hydrogen, halogen, cyano or C$_1$-C$_3$-alkyl, particularly preferably hydrogen
p is a number from 1 to 4;
X is a group —CH—R$^a$—, —N—R$^b$—, —O— or —S—; particularly preferably —CH—R$^a$—,
R$^a$ is hydrogen or C$_1$-C$_3$-alkyl;
o is 0;
Z is O, S, NH, NCH$_3$ or NOCH$_3$ and particularly preferably O or S.

In particular with a view to their use, preference is given to the compounds I compiled in the tables below. Moreover, the groups mentioned for a substituent in the tables are per se, independently of the combination in which they are mentioned, a particularly preferred embodiment of the substituent in question.

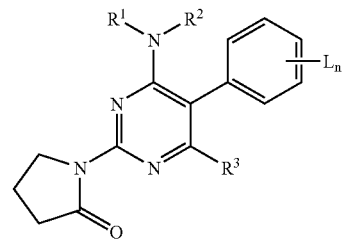

Ia

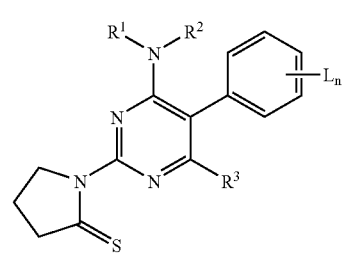

Ib

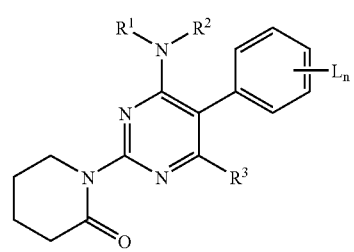

Ic

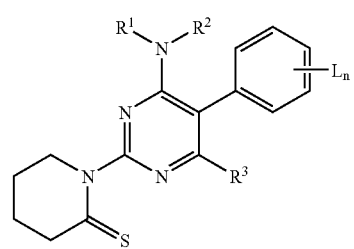

Id

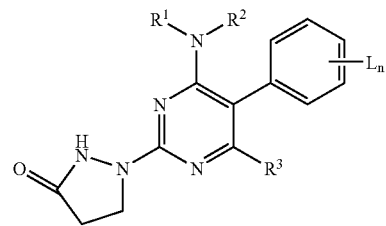

Ie

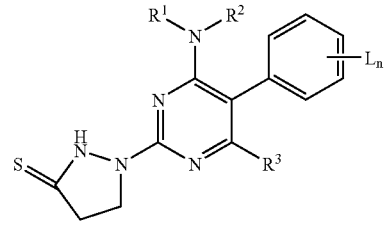

If

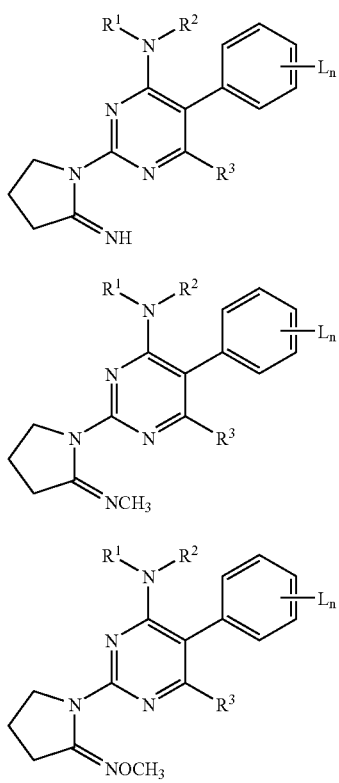

Ig

Ih

Ii

TABLE 1

Compounds of the formula Ia, Ib, Ic, Id, Ie, If, Ig, Ih and Ii in which $L_n$ is 2-fluoro,6-chloro, $R^3$ is methyl and $R^1$, $R^2$ for each compound corresponds to one row of Table A

TABLE 2

Compounds of the formula Ia, Ib, Ic, Id, Ie, If, Ig, Ih and Ii in which $L_n$ is 2,6-difluoro, $R^3$ is methyl and $R^1$, $R^2$ for each compound corresponds to one row of Table A

TABLE 3

Compounds of the formula Ia, Ib, Ic, Id, Ie, If, Ig, Ih and Ii in which $L_n$ is 2,6-dichloro, $R^3$ is methyl and $R^1$, $R^2$ for each compound corresponds to one row of Table A

TABLE 4

Compounds of the formula Ia, Ib, Ic, Id, Ie, If, Ig, Ih and Ii in which $L_n$ is 2-fluoro,6-methyl, $R^3$ is methyl and $R^1$, $R^2$ for each compound corresponds to one row of Table A

TABLE 5

Compounds of the formula Ia, Ib, Ic, Id, Ie, If, Ig, Ih and Ii in which $L_n$ is 2,4,6-trifluoro, $R^3$ is methyl and $R^1$, $R^2$ for each compound corresponds to one row of Table A

TABLE 6

Compounds of the formula Ia, Ib, Ic, Id, Ie, If, Ig, Ih and Ii in which $L_n$ is 2-methyl,4-fluoro, $R^3$ is methyl and $R^1$, $R^2$ for each compound corresponds to one row of Table A

TABLE 7

Compounds of the formula Ia, Ib, Ic, Id, Ie, If, Ig, Ih and Ii in which $L_n$ is 2-fluoro,4-methoxycarbonyl, $R^3$ is methyl and $R^1$, $R^2$ for each compound corresponds to one row of Table A

TABLE 8

Compounds of the formula Ia, Ib, Ic, Id, Ie, If, Ig, Ih and Ii in which $L_n$ is 2-fluoro,4-CN, $R^3$ is methyl and $R^1$, $R^2$ for each compound corresponds to one row of Table A

TABLE 9

Compounds of the formula Ia, Ib, Ic, Id, Ie, If, Ig, Ih and Ii in which $L_n$ is 2,4,5-trifluoro, $R^3$ is methyl and $R^1$, $R^2$ for each compound corresponds to one row of Table A

TABLE 10

Compounds of the formula Ia, Ib, Ic, Id, Ie, If, Ig, Ih and Ii in which $L_n$ is 2,4-dichloro, $R^3$ is methyl and $R^1$, $R^2$ for each compound corresponds to one row of Table A

TABLE 11

Compounds of the formula Ia, Ib, Ic, Id, Ie, If, Ig, Ih and Ii in which $L_n$ is 2-chloro, $R^3$ is methyl and $R^1$, $R^2$ for each compound corresponds to one row of Table A

TABLE 12

Compounds of the formula Ia, Ib, Ic, Id, Ie, If, Ig, Ih and Ii in which $L_n$ is 2-fluoro, $R^3$ is methyl and $R^1$, $R^2$ for each compound corresponds to one row of Table A

TABLE 13

Compounds of the formula Ia, Ib, Ic, Id, Ie, If, Ig, Ih and Ii in which $L_n$ is 2,4-difluoro, $R^3$ is methyl and $R^1$, $R^2$ for each compound corresponds to one row of Table A

TABLE 14

Compounds of the formula Ia, Ib, Ic, Id, Ie, If, Ig, Ih and Ii in which $L_n$ is 2-fluoro-4-chloro, $R^3$ is methyl and $R^1$, $R^2$ for each compound corresponds to one row of Table A

TABLE 15

Compounds of the formula Ia, Ib, Ic, Id, Ie, If, Ig, Ih and Ii in which $L_n$ is 2-chloro-4-fluoro, $R^3$ is methyl and $R^1$, $R^2$ for each compound corresponds to one row of Table A

TABLE 16

Compounds of the formula Ia, Ib, Ic, Id, Ie, If, Ig, Ih and Ii in which $L_n$ is 2,3-difluoro, $R^3$ is methyl and $R^1$, $R^2$ for each compound corresponds to one row of Table A

TABLE 17

Compounds of the formula Ia, Ib, Ic, Id, Ie, If, Ig, Ih and Ii in which $L_n$ is 2,5-difluoro, $R^3$ is methyl and $R^1$, $R^2$ for each compound corresponds to one row of Table A

TABLE 18

Compounds of the formula Ia, Ib, Ic, Id, Ie, If, Ig, Ih and Ii in which $L_n$ is 2,3,4-trifluoro, $R^3$ is methyl and $R^1$, $R^2$ for each compound corresponds to one row of Table A

TABLE 19

Compounds of the formula Ia, Ib, Ic, Id, Ie, If, Ig, Ih and Ii in which $L_n$ is 2-methyl, $R^3$ is methyl and $R^1$, $R^2$ for each compound corresponds to one row of Table A

TABLE 20

Compounds of the formula Ia, Ib, Ic, Id, Ie, If, Ig, Ih and Ii in which $L_n$ is 2,4-dimethyl, $R^3$ is methyl and $R^1$, $R^2$ for each compound corresponds to one row of Table A

TABLE 21

Compounds of the formula Ia, Ib, Ic, Id, Ie, If, Ig, Ih and Ii in which $L_n$ is 2-methyl-4-chloro, $R^3$ is methyl and $R^1$, $R^2$ for each compound corresponds to one row of Table A

TABLE 22

Compounds of the formula Ia, Ib, Ic, Id, Ie, If, Ig, Ih and Ii in which $L_n$ is 2-fluoro-4-methyl, $R^3$ is methyl and $R^1$, $R^2$ for each compound corresponds to one row of Table A

TABLE 23

Compounds of the formula Ia, Ib, Ic, Id, Ie, If, Ig, Ih and Ii in which $L_n$ is 2,6-dimethyl, $R^3$ is methyl and $R^1$, $R^2$ for each compound corresponds to one row of Table A

TABLE 24

Compounds of the formula Ia, Ib, Ic, Id, Ie, If, Ig, Ih and Ii in which $L_n$ is 2,4,6-trimethyl, $R^3$ is methyl and $R^1$, $R^2$ for each compound corresponds to one row of Table A

TABLE 25

Compounds of the formula Ia, Ib, Ic, Id, Ie, If, Ig, Ih and Ii in which $L_n$ is 2,6-difluoro-4-cyano, $R^3$ is methyl and $R^1$, $R^2$ for each compound corresponds to one row of Table A

TABLE 26

Compounds of the formula Ia, Ib, Ic, Id, Ie, If, Ig, Ih and Ii in which $L_n$ is 2,6-difluoro-4-methyl, $R^3$ is methyl and $R^1$, $R^2$ for each compound corresponds to one row of Table A

TABLE 27

Compounds of the formula Ia, Ib, Ic, Id, Ie, If, Ig, Ih and Ii in which $L_n$ is 2,6-difluoro-4-methoxycarbonyl, $R^3$ is methyl and $R^1$, $R^2$ for each compound corresponds to one row of Table A

TABLE 28

Compounds of the formula Ia, Ib, Ic, Id, Ie, If, Ig, Ih and Ii in which $L_n$ is 2-chloro,4-methoxy, $R^3$ is methyl and $R^1$, $R^2$ for each compound corresponds to one row of Table A

TABLE 29

Compounds of the formula Ia, Ib, Ic, Id, Ie, If, Ig, Ih and Ii in which $L_n$ is 2-chloro,4-methyl, $R^3$ is methyl and $R^1$, $R^2$ for each compound corresponds to one row of Table A

TABLE 30

Compounds of the formula Ia, Ib, Ic, Id, Ie, If, Ig, Ih and Ii in which $L_n$ is 2-chloro,4-methoxycarbonyl, $R^3$ is methyl and $R^1$, $R^2$ for each compound corresponds to one row of Table A

TABLE 31

Compounds of the formula Ia, Ib, Ic, Id, Ie, If, Ig, Ih and Ii in which $L_n$ is 2-chloro,4-bromo, $R^3$ is methyl and $R^1$, $R^2$ for each compound corresponds to one row of Table A

TABLE 32

Compounds of the formula Ia, Ib, Ic, Id, Ie, If, Ig, Ih and Ii in which $L_n$ is 2-chloro,4-cyano, $R^3$ is methyl and $R^1$, $R^2$ for each compound corresponds to one row of Table A

TABLE 33

Compounds of the formula Ia, Ib, Ic, Id, Ie, If, Ig, Ih and Ii in which $L_n$ is 2,6-difluoro,4-methoxy, $R^3$ is methyl and $R^1$, $R^2$ for each compound corresponds to one row of Table A

TABLE 34

Compounds of the formula Ia, Ib, Ic, Id, Ie, If, Ig, Ih and Ii in which $L_n$ is 2-fluoro,3-methyl, $R^3$ is methyl and $R^1$, $R^2$ for each compound corresponds to one row of Table A

TABLE 35

Compounds of the formula Ia, Ib, Ic, Id, Ie, If, Ig, Ih and Ii in which $L_n$ is 2,5-dimethyl, $R^3$ is methyl and $R^1$, $R^2$ for each compound corresponds to one row of Table A

TABLE 36

Compounds of the formula Ia, Ib, Ic, Id, Ie, If, Ig, Ih and Ii in which $L_n$ is 2-methyl,4-cyano, $R^3$ is methyl and $R^1$, $R^2$ for each compound corresponds to one row of Table A

TABLE 37

Compounds of the formula Ia, Ib, Ic, Id, Ie, If, Ig, Ih and Ii in which $L_n$ is 2-methyl,4-bromo, $R^3$ is methyl and $R^1$, $R^2$ for each compound corresponds to one row of Table A

TABLE 38

Compounds of the formula Ia, Ib, Ic, Id, Ie, If, Ig, Ih and Ii in which $L_n$ is 2-methyl,5-fluoro, $R^3$ is methyl and $R^1$, $R^2$ for each compound corresponds to one row of Table A

TABLE 39

Compounds of the formula Ia, Ib, Ic, Id, Ie, If, Ig, Ih and Ii in which $L_n$ is 2-methyl,4-methoxy, $R^3$ is methyl and $R^1$, $R^2$ for each compound corresponds to one row of Table A

TABLE 40

Compounds of the formula Ia, Ib, Ic, Id, Ie, If, Ig, Ih and Ii in which $L_n$ is 2-methyl,4-methoxycarbonyl, $R^3$ is methyl and $R^1$, $R^2$ for each compound corresponds to one row of Table A

TABLE 41

Compounds of the formula Ia, Ib, Ic, Id, Ie, If, Ig, Ih and Ii in which $L_n$ is 2,5-dimethyl,4-bromo, $R^3$ is methyl and $R^1$, $R^2$ for each compound corresponds to one row of Table A

TABLE 42

Compounds of the formula Ia, Ib, Ic, Id, Ie, If, Ig, Ih and Ii in which $L_n$ is 2-fluoro,4-bromo, $R^3$ is methyl and $R^1$, $R^2$ for each compound corresponds to one row of Table A

TABLE 43

Compounds of the formula Ia, Ib, Ic, Id, Ie, If, Ig, Ih and Ii in which $L_n$ is 2-fluoro,4-methoxy, $R^2$ is methyl and $R^1$, $R^2$ for each compound corresponds to one row of Table A

TABLE 44

Compounds of the formula Ia, Ib, Ic, Id, Ie, If, Ig, Ih and Ii in which $L_n$ is 2-fluoro,5-methyl, $R^3$ is methyl and $R^1$, $R^2$ for each compound corresponds to one row of Table A

TABLE 45

Compounds of the formula Ia, Ib, Ic, Id, Ie, If, Ig, Ih and Ii in which $L_n$ is pentafluoro, $R^3$ is methyl and $R^1$, $R^2$ for each compound corresponds to one row of Table A

TABLE 46

Compounds of the formula Ia, Ib, Ic, Id, Ie, If, Ig, Ih and Ii in which $L_n$ is 2-fluoro,6-chloro, $R^3$ is chlorine and $R^1$, $R^2$ for each compound corresponds to one row of Table A

TABLE 47

Compounds of the formula Ia, Ib, Ic, Id, Ie, If, Ig, Ih and Ii in which $L_n$ is 2,6-difluoro, $R^3$ is chlorine and $R^1$, $R^2$ for each compound corresponds to one row of Table A

TABLE 48

Compounds of the formula Ia, Ib, Ic, Id, Ie, If, Ig, Ih and Ii in which $L_n$ is 2,6-dichloro, $R^3$ is chlorine and $R^1$, $R^2$ for each compound corresponds to one row of Table A

TABLE 49

Compounds of the formula Ia, Ib, Ic, Id, Ie, If, Ig, Ih and Ii in which $L_n$ is 2-fluoro,6-methyl, $R^3$ is chlorine and $R^1$, $R^2$ for each compound corresponds to one row of Table A

TABLE 50

Compounds of the formula Ia, Ib, Ic, Id, Ie, If, Ig, Ih and Ii in which $L_n$ is 2,4,6-trifluoro, $R^3$ is chlorine and $R^1$, $R^2$ for each compound corresponds to one row of Table A

TABLE 51

Compounds of the formula Ia, Ib, Ic, Id, Ie, If, Ig, Ih and Ii in which $L_n$ is 2-methyl,4-fluoro, $R^3$ is chlorine and $R^1$, $R^2$ for each compound corresponds to one row of Table A

TABLE 52

Compounds of the formula Ia, Ib, Ic, Id, Ie, If, Ig, Ih and Ii in which $L_n$ is 2-fluoro,4-methoxycarbonyl, $R^3$ is chlorine and $R^1$, $R^2$ for each compound corresponds to one row of Table A

TABLE 53

Compounds of the formula Ia, Ib, Ic, Id, Ie, If, Ig, Ih and Ii in which $L_n$ is 2-fluoro,4-CN, $R^3$ is chlorine and $R^1$, $R^2$ for each compound corresponds to one row of Table A

TABLE 54

Compounds of the formula Ia, Ib, Ic, Id, Ie, If, Ig, Ih and Ii in which $L_n$ is 2,4,5-trifluoro, $R^3$ is chlorine and $R^1$, $R^2$ for each compound corresponds to one row of Table A

TABLE 55

Compounds of the formula Ia, Ib, Ic, Id, Ie, If, Ig, Ih and Ii in which $L_n$ is 2,4-dichloro, $R^3$ is chlorine and $R^1$, $R^2$ for each compound corresponds to one row of Table A

TABLE 56

Compounds of the formula Ia, Ib, Ic, Id, Ie, If, Ig, Ih and Ii in which $L_n$ is 2-chloro, $R^3$ is chlorine and $R^1$, $R^2$ for each compound corresponds to one row of Table A

TABLE 57

Compounds of the formula Ia, Ib, Ic, Id, Ie, If, Ig, Ih and Ii in which $L_n$ is 2-fluoro, $R^3$ is chlorine and $R^1$, $R^2$ for each compound corresponds to one row of Table A

TABLE 58

Compounds of the formula Ia, Ib, Ic, Id, Ie, If, Ig, Ih and Ii in which $L_n$ is 2,4-difluoro, $R^3$ is chlorine and $R^1$, $R^2$ for each compound corresponds to one row of Table A

TABLE 59

Compounds of the formula Ia, Ib, Ic, Id, Ie, If, Ig, Ih and Ii in which $L_n$ is 2-fluoro-4-chloro, $R^3$ is chlorine and $R^1$, $R^2$ for each compound corresponds to one row of Table A

TABLE 60

Compounds of the formula Ia, Ib, Ic, Id, Ie, If, Ig, Ih and Ii in which $L_n$ is 2-chloro-4-fluoro, $R^3$ is chlorine and $R^1$, $R^2$ for each compound corresponds to one row of Table A

TABLE 61

Compounds of the formula Ia, Ib, Ic, Id, Ie, If, Ig, Ih and Ii in which $L_n$ is 2,3-difluoro, $R^3$ is chlorine and $R^1$, $R^2$ for each compound corresponds to one row of Table A

TABLE 62

Compounds of the formula Ia, Ib, Ic, Id, Ie, If, Ig, Ih and Ii in which $L_n$ is 2,5-difluoro, $R^3$ is chlorine and $R^1$, $R^2$ for each compound corresponds to one row of Table A

TABLE 63

Compounds of the formula Ia, Ib, Ic, Id, Ie, If, Ig, Ih and Ii in which $L_n$ is 2,3,4-trifluoro, $R^3$ is chlorine and $R^1$, $R^2$ for each compound corresponds to one row of Table A

TABLE 64

Compounds of the formula Ia, Ib, Ic, Id, Ie, If, Ig, Ih and Ii in which $L_n$ is 2-methyl, $R^3$ is chlorine and $R^1$, $R^2$ for each compound corresponds to one row of Table A

TABLE 65

Compounds of the formula Ia, Ib, Ic, Id, Ie, If, Ig, Ih and Ii in which $L_n$ is 2,4-dimethyl, $R^3$ is chlorine and $R^1$, $R^2$ for each compound corresponds to one row of Table A

TABLE 66

Compounds of the formula Ia, Ib, Ic, Id, Ie, If, Ig, Ih and Ii in which $L_n$ is 2-methyl-4-chloro, $R^3$ is chlorine and $R^1$, $R^2$ for each compound corresponds to one row of Table A

TABLE 67

Compounds of the formula Ia, Ib, Ic, Id, Ie, If, Ig, Ih and Ii in which $L_n$ is 2-fluoro-4-methyl, $R^2$ is chlorine and $R^1$, $R^2$ for each compound corresponds to one row of Table A

TABLE 68

Compounds of the formula Ia, Ib, Ic, Id, Ie, If, Ig, Ih and Ii in which $L_n$ is 2,6-dimethyl, $R^3$ is chlorine and $R^1$, $R^2$ for each compound corresponds to one row of Table A

TABLE 69

Compounds of the formula Ia, Ib, Ic, Id, Ie, If, Ig, Ih and Ii in which $L_n$ is 2,4,6-trimethyl, $R^3$ is chlorine and $R^1$, $R^2$ for each compound corresponds to one row of Table A

TABLE 70

Compounds of the formula Ia, Ib, Ic, Id, Ie, If, Ig, Ih and Ii in which $L_n$ is 2,6-difluoro-4-cyano, $R^3$ is chlorine and $R^1$, $R^2$ for each compound corresponds to one row of Table A

TABLE 71

Compounds of the formula Ia, Ib, Ic, Id, Ie, If, Ig, Ih and Ii in which $L_n$ is 2,6-difluoro-4-methyl, $R^3$ is chlorine and $R^1$, $R^2$ for each compound corresponds to one row of Table A

TABLE 72

Compounds of the formula Ia, Ib, Ic, Id, Ie, If, Ig, Ih and Ii in which $L_n$ is 2,6-difluoro-4-methoxycarbonyl, $R^3$ is chlorine and $R^1$, $R^2$ for each compound corresponds to one row of Table A

TABLE 73

Compounds of the formula Ia, Ib, Ic, Id, Ie, If, Ig, Ih and Ii in which $L_n$ is 2-chloro,4-methoxy, $R^3$ is chlorine and $R^1$, $R^2$ for each compound corresponds to one row of Table A

TABLE 74

Compounds of the formula Ia, Ib, Ic, Id, Ie, If, Ig, Ih and Ii in which $L_n$ is 2-chloro,4-methyl, $R^3$ is chlorine and $R^1$, $R^2$ for each compound corresponds to one row of Table A

TABLE 75

Compounds of the formula Ia, Ib, Ic, Id, Ie, If, Ig, Ih and Ii in which $L_n$ is 2-chloro,4-methoxycarbonyl, $R^3$ is chlorine and $R^1$, $R^2$ for each compound corresponds to one row of Table A

TABLE 76

Compounds of the formula Ia, Ib, Ic, Id, Ie, If, Ig, Ih and Ii in which $L_n$ is 2-chloro,4-bromo, $R^3$ is chlorine and $R^1$, $R^2$ for each compound corresponds to one row of Table A

TABLE 77

Compounds of the formula Ia, Ib, Ic, Id, Ie, If, Ig, Ih and Ii in which $L_n$ is 2-chloro,4-cyano, $R^3$ is chlorine and $R^1$, $R^2$ for each compound corresponds to one row of Table A

TABLE 78

Compounds of the formula Ia, Ib, Ic, Id, Ie, If, Ig, Ih and Ii in which $L_n$ is 2,6-difluoro,4-methoxy, $R^3$ is chlorine and $R^1$, $R^2$ for each compound corresponds to one row of Table A

TABLE 79

Compounds of the formula Ia, Ib, Ic, Id, Ie, If, Ig, Ih and Ii in which $L_n$ is 2-fluoro,3-methyl, $R^3$ is chlorine and $R^1$, $R^2$ for each compound corresponds to one row of Table A

TABLE 80

Compounds of the formula Ia, Ib, Ic, Id, Ie, If, Ig, Ih and Ii in which $L_n$ is 2,5-dimethyl, $R^3$ is chlorine and $R^1$, $R^2$ for each compound corresponds to one row of Table A

TABLE 81

Compounds of the formula Ia, Ib, Ic, Id, Ie, If, Ig, Ih and Ii in which $L_n$ is 2-methyl,4-cyano, $R^3$ is chlorine and $R^1$, $R^2$ for each compound corresponds to one row of Table A

TABLE 82

Compounds of the formula Ia, Ib, Ic, Id, Ie, If, Ig, Ih and Ii in which $L_n$ is 2-methyl,4-bromo, $R^3$ is chlorine and $R^1$, $R^2$ for each compound corresponds to one row of Table A

TABLE 83

Compounds of the formula Ia, Ib, Ic, Id, Ie, If, Ig, Ih and Ii in which $L_n$ is 2-methyl,5-fluoro, $R^3$ is chlorine and $R^1$, $R^2$ for each compound corresponds to one row of Table A

TABLE 84

Compounds of the formula Ia, Ib, Ic, Id, Ie, If, Ig, Ih and Ii in which $L_n$ is 2-methyl,4-methoxy, $R^3$ is chlorine and $R^1$, $R^2$ for each compound corresponds to one row of Table A

TABLE 85

Compounds of the formula Ia, Ib, Ic, Id, Ie, If, Ig, Ih and Ii in which $L_n$ is 2-methyl,4-methoxycarbonyl, $R^3$ is chlorine and $R^1$, $R^2$ for each compound corresponds to one row of Table A

TABLE 86

Compounds of the formula Ia, Ib, Ic, Id, Ie, If, Ig, Ih and Ii in which $L_n$ is 2,5-dimethyl,4-bromo, $R^3$ is chlorine and $R^1$, $R^2$ for each compound corresponds to one row of Table A

TABLE 87

Compounds of the formula Ia, Ib, Ic, Id, Ie, If, Ig, Ih and Ii in which $L_n$ is 2-fluoro,4-bromo, $R^3$ is chlorine and $R^1$, $R^2$ for each compound corresponds to one row of Table A

TABLE 88

Compounds of the formula Ia, Ib, Ic, Id, Ie, If, Ig, Ih and Ii in which $L_n$ is 2-fluoro,4-methoxy, $R^3$ is chlorine and $R^1$, $R^2$ for each compound corresponds to one row of Table A

TABLE 89

Compounds of the formula Ia, Ib, Ic, Id, Ie, If, Ig, Ih and Ii in which $L_n$ is 2-fluoro,5-methyl, $R^3$ is chlorine and $R^1$, $R^2$ for each compound corresponds to one row of Table A

TABLE 90

Compounds of the formula Ia, Ib, Ic, Id, Ie, If, Ig, Ih and Ii in which $L_n$ is pentafluoro, $R^3$ is chlorine and $R^1$, $R^2$ for each compound corresponds to one row of Table A

TABLE 91

Compounds of the formula Ia, Ib, Ic, Id, Ie, If, Ig, Ih and Ii in which $L_n$ is 2-fluoro,6-chloro, $R^3$ is methoxy and $R^1$, $R^2$ for each compound corresponds to one row of Table A

TABLE 92

Compounds of the formula Ia, Ib, Ic, Id, Ie, If, Ig, Ih and Ii in which $L_n$ is 2,6-difluoro, $R^3$ is methoxy and $R^1$, $R^2$ for each compound corresponds to one row of Table A

TABLE 93

Compounds of the formula Ia, Ib, Ic, Id, Ie, If, Ig, Ih and Ii in which $L_n$ is 2,6-dichloro, $R^3$ is methoxy and $R^1$, $R^2$ for each compound corresponds to one row of Table A

TABLE 94

Compounds of the formula Ia, Ib, Ic, Id, Ie, If, Ig, Ih and Ii in which $L_n$ is 2-fluoro,6-methyl, $R^3$ is methoxy and $R^1$, $R^2$ for each compound corresponds to one row of Table A

TABLE 95

Compounds of the formula Ia, Ib, Ic, Id, Ie, If, Ig, Ih and Ii in which $L_n$ is 2,4,6-trifluoro, $R^3$ is methoxy and $R^1$, $R^2$ for each compound corresponds to one row of Table A

TABLE 96

Compounds of the formula la, lb, lc, ld, le, lf, lg, lh and li in which $L_n$ is 2-methyl,4-fluoro, $R^3$ is methoxy and $R^1$, $R^2$ for each compound corresponds to one row of Table A

TABLE 97

Compounds of the formula la, lb, lc, ld, le, lf, lg, lh and li in which $L_n$ is 2-fluoro,4-methoxycarbonyl, $R^3$ is methoxy and $R^1$, $R^2$ for each compound corresponds to one row of Table A

TABLE 98

Compounds of the formula la, lb, lc, ld, le, lf, lg, lh and li in which $L_n$ is 2-fluoro,4-CN, $R^3$ is methoxy and $R^1$, $R^2$ for each compound corresponds to one row of Table A

TABLE 99

Compounds of the formula la, lb, lc, ld, le, lf, lg, lh and li in which $L_n$ is 2,4,5-trifluoro, $R^3$ is methoxy and $R^1$, $R^2$ for each compound corresponds to one row of Table A

TABLE 100

Compounds of the formula la, lb, lc, ld, le, lf, lg, lh and li in which $L_n$ is 2,4-dichloro, $R^3$ is methoxy and $R^1$, $R^2$ for each compound corresponds to one row of Table A

TABLE 101

Compounds of the formula la, lb, lc, ld, le, lf, lg, lh and li in which $L_n$ is 2-chloro, $R^3$ is methoxy and $R^1$, $R^2$ for each compound corresponds to one row of Table A

TABLE 102

Compounds of the formula la, lb, lc, ld, le, lf, lg, lh and li in which $L_n$ is 2-fluoro, $R^3$ is methoxy and $R^1$, $R^2$ for each compound corresponds to one row of Table A

TABLE 103

Compounds of the formula la, lb, lc, ld, le, lf, lg, lh and li in which $L_n$ is 2,4-difluoro, $R^3$ is methoxy and $R^1$, $R^2$ for each compound corresponds to one row of Table A

TABLE 104

Compounds of the formula la, lb, lc, ld, le, lf, lg, lh and li in which $L_n$ is 2-fluoro-4-chloro, $R^3$ is methoxy and $R^1$, $R^2$ for each compound corresponds to one row of Table A

TABLE 105

Compounds of the formula la, lb, lc, ld, le, lf, lg, lh and li in which $L_n$ is 2-chloro-4-fluoro, $R^3$ is methoxy and $R^1$, $R^2$ for each compound corresponds to one row of Table A

TABLE 106

Compounds of the formula la, lb, lc, ld, le, lf, lg, lh and li in which $L_n$ is 2,3-difluoro, $R^3$ is methoxy and $R^1$, $R^2$ for each compound corresponds to one row of Table A

TABLE 107

Compounds of the formula la, lb, lc, ld, le, lf, lg, lh and li in which $L_n$ is 2,5-difluoro, $R^3$ is methoxy and $R^1$, $R^2$ for each compound corresponds to one row of Table A

TABLE 108

Compounds of the formula la, lb, lc, ld, le, lf, lg, lh and li in which $L_n$ is 2,3,4-trifluoro, $R^3$ is methoxy and $R^1$, $R^2$ for each compound corresponds to one row of Table A

TABLE 109

Compounds of the formula la, lb, lc, ld, le, lf, lg, lh and li in which $L_n$ is 2-methyl, $R^3$ is methoxy and $R^1$, $R^2$ for each compound corresponds to one row of Table A

TABLE 110

Compounds of the formula la, lb, lc, ld, le, lf, lg, lh and li in which $L_n$ is 2,4-dimethyl, $R^3$ is methoxy and $R^1$, $R^2$ for each compound corresponds to one row of Table A

TABLE 111

Compounds of the formula la, lb, lc, ld, le, lf, lg, lh and li in which $L_n$ is 2-methyl-4-chloro, $R^3$ is methoxy and $R^1$, $R^2$ for each compound corresponds to one row of Table A

TABLE 112

Compounds of the formula la, lb, lc, ld, le, lf, lg, lh and li in which $L_n$ is 2-fluoro-4-methyl, $R^3$ is methoxy and $R^1$, $R^2$ for each compound corresponds to one row of Table A

TABLE 113

Compounds of the formula la, lb, lc, ld, le, lf, lg, lh and li in which $L_n$ is 2,6-dimethyl, $R^3$ is methoxy and $R^1$, $R^2$ for each compound corresponds to one row of Table A

TABLE 114

Compounds of the formula la, lb, lc, ld, le, lf, lg, lh and li in which $L_n$ is 2,4,6-trimethyl, $R^3$ is methoxy and $R^1$, $R^2$ for each compound corresponds to one row of Table A

TABLE 115

Compounds of the formula la, lb, lc, ld, le, lf, lg, lh and li in which $L_n$ is 2,6-difluoro-4-cyano, $R^3$ is methoxy and $R^1$, $R^2$ for each compound corresponds to one row of Table A

TABLE 116

Compounds of the formula Ia, Ib, Ic, Id, Ie, If, Ig, Ih and Ii in which $L_n$ is 2,6-difluoro-4-methyl, $R^3$ is methoxy and $R^1$, $R^2$ for each compound corresponds to one row of Table A

TABLE 117

Compounds of the formula Ia, Ib, Ic, Id, Ie, If, Ig, Ih and Ii in which $L_n$ is 2,6-difluoro-4-methoxycarbonyl, $R^3$ is methoxy and $R^1$, $R^2$ for each compound corresponds to one row of Table A

TABLE 118

Compounds of the formula Ia, Ib, Ic, Id, Ie, If, Ig, Ih and Ii in which $L_n$ is 2-chloro,4-methoxy, $R^3$ is methoxy and $R^1$, $R^2$ for each compound corresponds to one row of Table A

TABLE 119

Compounds of the formula Ia, Ib, Ic, Id, Ie, If, Ig, Ih and Ii in which $L_n$ is 2-chloro,4-methyl, $R^3$ is methoxy and $R^1$, $R^2$ for each compound corresponds to one row of Table A

TABLE 120

Compounds of the formula Ia, Ib, Ic, Id, Ie, If, Ig, Ih and Ii in which $L_n$ is 2-chloro,4-methoxycarbonyl, $R^3$ is methoxy and $R^1$, $R^2$ for each compound corresponds to one row of Table A

TABLE 121

Compounds of the formula Ia, Ib, Ic, Id, Ie, If, Ig, Ih and Ii in which $L_n$ is 2-chloro,4-methoxy, $R^3$ is methoxy and $R^1$, $R^2$ for each compound corresponds to one row of Table A

TABLE 122

Compounds of the formula Ia, Ib, Ic, Id, Ie, If, Ig, Ih and Ii in which $L_n$ is 2-chloro,4-cyano, $R^3$ is methoxy and $R^1$, $R^2$ for each compound corresponds to one row of Table A

TABLE 123

Compounds of the formula Ia, Ib, Ic, Id, Ie, If, Ig, Ih and Ii in which $L_n$ is 2,6-difluoro,4-methoxy, $R^3$ is methoxy and $R^1$, $R^2$ for each compound corresponds to one row of Table A

TABLE 124

Compounds of the formula Ia, Ib, Ic, Id, Ie, If, Ig, Ih and Ii in which $L_n$ is 2-fluoro,3-methyl, $R^3$ is methoxy and $R^1$, $R^2$ for each compound corresponds to one row of Table A

TABLE 125

Compounds of the formula Ia, Ib, Ic, Id, Ie, If, Ig, Ih and Ii in which $L_n$ is 2,5-dimethyl, $R^3$ is methoxy and $R^1$, $R^2$ for each compound corresponds to one row of Table A

TABLE 126

Compounds of the formula Ia, Ib, Ic, Id, Ie, If, Ig, Ih and Ii in which $L_n$ is 2-methyl,4-cyano, $R^3$ is methoxy and $R^1$, $R^2$ for each compound corresponds to one row of Table A

TABLE 127

Compounds of the formula Ia, Ib, Ic, Id, Ie, If, Ig, Ih and Ii in which $L_n$ is 2-methyl,4-bromo, $R^3$ is methoxy and $R^1$, $R^2$ for each compound corresponds to one row of Table A

TABLE 128

Compounds of the formula Ia, Ib, Ic, Id, Ie, If, Ig, Ih and Ii in which $L_n$ is 2-methyl,5-fluoro, $R^3$ is methoxy and $R^1$, $R^2$ for each compound corresponds to one row of Table A

TABLE 129

Compounds of the formula Ia, Ib, Ic, Id, Ie, If, Ig, Ih and Ii in which $L_n$ is 2-methyl,4-methoxy, $R^3$ is methoxy and $R^1$, $R^2$ for each compound corresponds to one row of Table A

TABLE 130

Compounds of the formula Ia, Ib, Ic, Id, Ie, If, Ig, Ih and Ii in which $L_n$ is 2-methyl,4-methoxycarbonyl, $R^3$ is methoxy and $R^1$, $R^2$ for each compound corresponds to one, row of Table A

TABLE 131

Compounds of the formula Ia, Ib, Ic, Id, Ie, If, Ig, Ih and Ii in which $L_n$ is 2,5-dimethyl,4-bromo, $R^3$ is methoxy and $R^1$, $R^2$ for each compound corresponds to one row of Table A

TABLE 132

Compounds of the formula Ia, Ib, Ic, Id, Ie, If, Ig, Ih and Ii in which $L_n$ is 2-fluoro,4-bromo, $R^3$ is methoxy and $R^1$, $R^2$ for each compound corresponds to one row of Table A

TABLE 133

Compounds of the formula Ia, Ib, Ic, Id, Ie, If, Ig, Ih and Ii in which $L_n$ is 2-fluoro,4-methoxy, $R^3$ is methoxy and $R^1$, $R^2$ for each compound corresponds to one row of Table A

TABLE 134

Compounds of the formula Ia, Ib, Ic, Id, Ie, If, Ig, Ih and Ii in which $L_n$ is 2-fluoro,5-methyl, $R^3$ is methoxy and $R^1$, $R^2$ for each compound corresponds to one row of Table A

TABLE 135

Compounds of the formula Ia, Ib, Ic, Id, Ie, If, Ig, Ih and Ii in which $L_n$ is pentafluoro, $R^3$ is methoxy and $R^1$, $R^2$ for each compound corresponds to one row of Table A

TABLE 136

Compounds of the formula Ia, Ib, Ic, Id, Ie, If, Ig, Ih and Ii in which $L_n$ is 2-fluoro,6-chloro, $R^3$ is cyano and $R^1$, $R^2$ for each compound corresponds to one row of Table A

TABLE 137

Compounds of the formula Ia, Ib, Ic, Id, Ie, If, Ig, Ih and Ii in which $L_n$ is 2,6-difluoro, $R^3$ is cyano and $R^1$, $R^2$ for each compound corresponds to one row of Table A

TABLE 138

Compounds of the formula Ia, Ib, Ic, Id, Ie, If, Ig, Ih and Ii in which $L_n$ is 2,6-dichloro, $R^3$ is cyano and $R^1$, $R^2$ for each compound corresponds to one row of Table A

TABLE 139

Compounds of the formula Ia, Ib, Ic, Id, Ie, If, Ig, Ih and Ii in which $L_n$ is 2-fluoro,6-methyl, $R^3$ is cyano and $R^1$, $R^2$ for each compound corresponds to one row of Table A

TABLE 140

Compounds of the formula Ia, Ib, Ic, Id, Ie, If, Ig, Ih and Ii in which $L_n$ is 2,4,6-trifluoro, $R^3$ is cyano and $R^1$, $R^2$ for each compound corresponds to one row of Table A

TABLE 141

Compounds of the formula Ia, Ib, Ic, Id, Ie, If, Ig, Ih and Ii in which $L_n$ is 2-methyl,4-fluoro, $R^3$ is cyano and $R^1$, $R^2$ for each compound corresponds to one row of Table A

TABLE 142

Compounds of the formula Ia, Ib, Ic, Id, Ie, If, Ig, Ih and Ii in which $L_n$ is 2-fluoro,4-methoxycarbonyl, $R^3$ is cyano and $R^1$, $R^2$ for each compound corresponds to one row of Table A

TABLE 143

Compounds of the formula Ia, Ib, Ic, Id, Ie, If, Ig, Ih and Ii in which $L_n$ is 2-fluoro,4-CN, $R^3$ is cyano and $R^1$, $R^2$ for each compound corresponds to one row of Table A

TABLE 144

Compounds of the formula Ia, Ib, Ic, Id, Ie, If, Ig, Ih and Ii in which $L_n$ is 2,4,5-trifluoro, $R^3$ is cyano and $R^1$, $R^2$ for each compound corresponds to one row of Table A

TABLE 145

Compounds of the formula Ia, Ib, Ic, Id, Ie, If, Ig, Ih and Ii in which $L_n$ is 2,4-dichloro, $R^3$ is cyano and $R^1$, $R^2$ for each compound corresponds to one row of Table A

TABLE 146

Compounds of the formula Ia, Ib, Ic, Id, Ie, If, Ig, Ih and Ii in which $L_n$ is 2-chloro, $R^3$ is cyano and $R^1$, $R^2$ for each compound corresponds to one row of Table A

TABLE 147

Compounds of the formula Ia, Ib, Ic, Id, Ie, If, Ig, Ih and Ii in which $L_n$ is 2-fluoro, $R^3$ is cyano and $R^1$, $R^2$ for each compound corresponds to one row of Table A

TABLE 148

Compounds of the formula Ia, Ib, Ic, Id, Ie, If, Ig, Ih and Ii in which $L_n$ is 2,4-difluoro, $R^3$ is cyano and $R^1$, $R^2$ for each compound corresponds to one row of Table A

TABLE 149

Compounds of the formula Ia, Ib, Ic, Id, Ie, If, Ig, Ih and Ii in which $L_n$ is 2-fluoro-4-chloro, $R^3$ is cyano and $R^1$, $R^2$ for each compound corresponds to one row of Table A

TABLE 150

Compounds of the formula Ia, Ib, Ic, Id, Ie, If, Ig, Ih and Ii in which $L_n$ is 2-chloro-4-fluoro, $R^3$ is cyano and $R^1$, $R^2$ for each compound corresponds to one row of Table A

TABLE 151

Compounds of the formula Ia, Ib, Ic, Id, Ie, If, Ig, Ih and Ii in which $L_n$ is 2,3-difluoro, $R^3$ is cyano and $R^1$, $R^2$ for each compound corresponds to one row of Table A

TABLE 152

Compounds of the formula Ia, Ib, Ic, Id, Ie, If, Ig, Ih and Ii in which $L_n$ is 2,5-difluoro, $R^3$ is cyano and $R^1$, $R^2$ for each compound corresponds to one row of Table A

TABLE 153

Compounds of the formula Ia, Ib, Ic, Id, Ie, If, Ig, Ih and Ii in which $L_n$ is 2,3,4-trifluoro, $R^3$ is cyano and $R^1$, $R^2$ for each compound corresponds to one row of Table A

TABLE 154

Compounds of the formula Ia, Ib, Ic, Id, Ie, If, Ig, Ih and Ii in which $L_n$ is 2-methyl, $R^3$ is cyano and $R^1$, $R^2$ for each compound corresponds to one row of Table A

TABLE 155

Compounds of the formula Ia, Ib, Ic, Id, Ie, If, Ig, Ih and Ii in which $L_n$ is 2,4-dimethyl, $R^3$ is cyano and $R^1$, $R^2$ for each compound corresponds to one row of Table A

TABLE 156

Compounds of the formula Ia, Ib, Ic, Id, Ie, If, Ig, Ih and Ii in which $L_n$ is 2-methyl-4-chloro, $R^3$ is cyano and $R^1$, $R^2$ for each compound corresponds to one row of Table A

TABLE 157

Compounds of the formula Ia, Ib, Ic, Id, Ie, If, Ig, Ih and Ii in which $L_n$ is 2-fluoro-4-methyl, $R^3$ is cyano and $R^1$, $R^2$ for each compound corresponds to one row of Table A

TABLE 158

Compounds of the formula Ia, Ib, Ic, Id, Ie, If, Ig, Ih and Ii in which $L_n$ is 2,6-dimethyl, $R^3$ is cyano and $R^1$, $R^2$ for each compound corresponds to one row of Table A

TABLE 159

Compounds of the formula Ia, Ib, Ic, Id, Ie, If, Ig, Ih and Ii in which $L_n$ is 2,4,6-trimethyl, $R^3$ is cyano and $R^1$, $R^2$ for each compound corresponds to one row of Table A

TABLE 160

Compounds of the formula Ia, Ib, Ic, Id, Ie, If, Ig, Ih and Ii in which $L_n$ is 2,6-difluoro-4-cyano, $R^3$ is cyano and $R^1$, $R^2$ for each compound corresponds to one row of Table A

TABLE 161

Compounds of the formula Ia, Ib, Ic, Id, Ie, If, Ig, Ih and Ii in which $L_n$ is 2,6-difluoro-4-methyl, $R^3$ is cyano and $R^1$, $R^2$ for each compound corresponds to one row of Table A

TABLE 162

Compounds of the formula Ia, Ib, Ic, Id, Ie, If, Ig, Ih and Ii in which $L_n$ is 2,6-difluoro-4-methoxycarbonyl, $R^3$ is cyano and $R^1$, $R^2$ for each compound corresponds to one row of Table A

TABLE 163

Compounds of the formula Ia, Ib, Ic, Id, Ie, If, Ig, Ih and Ii in which $L_n$ is 2-chloro,4-methoxy, $R^3$ is cyano and $R^1$, $R^2$ for each compound corresponds to one row of Table A

TABLE 164

Compounds of the formula Ia, Ib, Ic, Id, Ie, If, Ig, Ih and Ii in which $L_n$ is 2-chloro,4-methyl, $R^3$ is cyano and $R^1$, $R^2$ for each compound corresponds to one row of Table A

TABLE 165

Compounds of the formula Ia, Ib, Ic, Id, Ie, If, Ig, Ih and Ii in which $L_n$ is 2-chloro,4-methoxycarbonyl, $R^3$ is cyano and $R^1$, $R^2$ for each compound corresponds to one row of Table A

TABLE 166

Compounds of the formula Ia, Ib, Ic, Id, Ie, If, Ig, Ih and Ii in which $L_n$ is 2-chloro,4-bromo, $R^3$ is cyano and $R^1$, $R^2$ for each compound corresponds to one row of Table A

TABLE 167

Compounds of the formula Ia, Ib, Ic, Id, Ie, If, Ig, Ih and Ii in which $L_n$ is 2-chloro,4-cyano, $R^3$ is cyano and $R^1$, $R^2$ for each compound corresponds to one row of Table A

TABLE 168

Compounds of the formula Ia, Ib, Ic, Id, Ie, If, Ig, Ih and Ii in which $L_n$ is 2,6-difluoro,4-methoxy, $R^3$ is cyano and $R^1$, $R^2$ for each compound corresponds to one row of Table A

TABLE 169

Compounds of the formula Ia, Ib, Ic, Id, Ie, If, Ig, Ih and Ii in which $L_n$ is 2-fluoro,3-methyl, $R^3$ is cyano and $R^1$, $R^2$ for each compound corresponds to one row of Table A

TABLE 170

Compounds of the formula Ia, Ib, Ic, Id, Ie, If, Ig, Ih and Ii in which $L_n$ is 2,5-dimethyl, $R^3$ is cyano and $R^1$, $R^2$ for each compound corresponds to one row of Table A

TABLE 171

Compounds of the formula Ia, Ib, Ic, Id, Ie, If, Ig, Ih and Ii in which $L_n$ is 2-methyl,4-cyano, $R^3$ is cyano and $R^1$, $R^2$ for each compound corresponds to one row of Table A

TABLE 172

Compounds of the formula Ia, Ib, Ic, Id, Ie, If, Ig, Ih and Ii in which $L_n$ is 2-methyl,4-bromo, $R^3$ is cyano and $R^1$, $R^2$ for each compound corresponds to one row of Table A

TABLE 173

Compounds of the formula Ia, Ib, Ic, Id, Ie, If, Ig, Ih and Ii in which $L_n$ is 2-methyl,5-fluoro, $R^3$ is cyano and $R^1$, $R^2$ for each compound corresponds to one row of Table A

TABLE 174

Compounds of the formula Ia, Ib, Ic, Id, Ie, If, Ig, Ih and Ii in which $L_n$ is 2-methyl,4-methoxy, $R^3$ is cyano and $R^1$, $R^2$ for each compound corresponds to one row of Table A

TABLE 175

Compounds of the formula Ia, Ib, Ic, Id, Ie, If, Ig, Ih and Ii in which $L_n$ is 2-methyl,4-methoxycarbonyl, $R^3$ is cyano and $R^1$, $R^2$ for each compound corresponds to one row of Table A

TABLE 176

Compounds of the formula Ia, Ib, Ic, Id, Ie, If, Ig, Ih and Ii in which $L_n$ is 2,5-dimethyl,4-bromo, $R^3$ is cyano and $R^1$, $R^2$ for each compound corresponds to one row of Table A

TABLE 177

Compounds of the formula Ia, Ib, Ic, Id, Ie, If, Ig, Ih and Ii in which $L_n$ is 2-fluoro,4-bromo, $R^3$ is cyano and $R^1$, $R^2$ for each compound corresponds to one row of Table A

TABLE 178

Compounds of the formula Ia, Ib, Ic, Id, Ie, If, Ig, Ih and Ii in which $L_n$ is 2-fluoro,4-methoxy, $R^3$ is cyano and $R^1$, $R^2$ for each compound corresponds to one row of Table A

TABLE 179

Compounds of the formula Ia, Ib, Ic, Id, Ie, If, Ig, Ih and Ii in which $L_n$ is 2-fluoro,5-methyl, $R^3$ is cyano and $R^1$, $R^2$ for each compound corresponds to one row of Table A

TABLE 180

Compounds of the formula Ia, Ib, Ic, Id, Ie, If, Ig, Ih and Ii in which $L_n$ is pentafluoro, $R^3$ is cyano and $R^1$, $R^2$ for each compound corresponds to one row of Table A

TABLE A

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CH_2CH_3$ | H |
| A-5 | $CH_2CH_2CH_3$ | $CH_3$ |
| A-6 | $CH_2CH_2CH_3$ | $CH_2CH_3$ |
| A-7 | $CH_2CH_2CH_3$ | $CH_2CH_2CH_3$ |
| A-8 | $CH_2CH_2F$ | H |
| A-9 | $CH_2CH_2F$ | $CH_3$ |
| A-10 | $CH_2CH_2F$ | $CH_2CH_3$ |
| A-11 | $CH_2CF_3$ | H |
| A-12 | $CH_2CF_3$ | $CH_3$ |
| A-13 | $CH_2CF_3$ | $CH_2CH_3$ |
| A-14 | $CH_2CF_3$ | $CH_2CH_2CH_3$ |
| A-15 | $CH_2CCl_3$ | H |
| A-16 | $CH_2CCl_3$ | $CH_3$ |
| A-17 | $CH_2CCl_3$ | $CH_2CH_3$ |
| A-18 | $CH_2CCl_3$ | $CH_2CH_2CH_3$ |
| A-19 | $CH(CH_3)_2$ | H |
| A-20 | $CH(CH_3)_2$ | $CH_3$ |
| A-21 | $CH(CH_3)_2$ | $CH_2CH_3$ |
| A-22 | $CH(CH_3)_2$ | $CH_2CH_2CH_3$ |
| A-23 | $CH_2C(CH_3)_3$ | H |
| A-24 | $CH_2C(CH_3)_3$ | $CH_3$ |
| A-25 | $CH_2C(CH_3)_3$ | $CH_2CH_3$ |
| A-26 | $CH_2CH(CH_3)_2$ | H |
| A-27 | $CH_2CH(CH_3)_2$ | $CH_3$ |
| A-28 | $CH_2CH(CH_3)_2$ | $CH_2CH_3$ |
| A-29 | (±) $CH(CH_2CH_3)CH_3$ | H |
| A-30 | (±) $CH(CH_2CH_3)CH_3$ | $CH_3$ |
| A-31 | (±) $CH(CH_2CH_3)CH_3$ | $CH_2CH_3$ |
| A-32 | (R) $CH(CH_2CH_3)CH_3$ | H |
| A-33 | (R) $CH(CH_2CH_3)CH_3$ | $CH_3$ |
| A-34 | (R) $CH(CH_2CH_3)CH_3$ | $CH_2CH_3$ |
| A-35 | (S) $CH(CH_2CH_3)CH_3$ | H |
| A-36 | (S) $CH(CH_2CH_3)CH_3$ | $CH_3$ |
| A-37 | (S) $CH(CH_2CH_3)CH_3$ | $CH_2CH_3$ |
| A-38 | (±) $CH(CH_3)—CH(CH_3)_2$ | H |
| A-39 | (±) $CH(CH_3)—CH(CH_3)_2$ | $CH_3$ |
| A-40 | (±) $CH(CH_3)—CH(CH_3)_2$ | $CH_2CH_3$ |
| A-41 | (R) $CH(CH_3)—CH(CH_3)_2$ | H |
| A-42 | (R) $CH(CH_3)—CH(CH_3)_2$ | $CH_3$ |
| A-43 | (R) $CH(CH_3)—CH(CH_3)_2$ | $CH_2CH_3$ |
| A-44 | (S) $CH(CH_3)—CH(CH_3)_2$ | H |
| A-45 | (S) $CH(CH_3)—CH(CH_3)_2$ | $CH_3$ |
| A-46 | (S) $CH(CH_3)—CH(CH_3)_2$ | $CH_2CH_3$ |
| A-47 | (±) $CH(CH_3)—C(CH_3)_3$ | H |
| A-48 | (±) $CH(CH_3)—C(CH_3)_3$ | $CH_3$ |
| A-49 | (±) $CH(CH_3)—C(CH_3)_3$ | $CH_2CH_3$ |
| A-50 | (R) $CH(CH_3)—C(CH_3)_3$ | H |
| A-51 | (R) $CH(CH_3)—C(CH_3)_3$ | $CH_3$ |
| A-52 | (R) $CH(CH_3)—C(CH_3)_3$ | $CH_2CH_3$ |
| A-53 | (S) $CH(CH_3)—C(CH_3)_3$ | H |
| A-54 | (S) $CH(CH_3)—C(CH_3)_3$ | $CH_3$ |
| A-55 | (S) $CH(CH_3)—C(CH_3)_3$ | $CH_2CH_3$ |
| A-56 | (±) $CH(CH_3)—CF_3$ | H |
| A-57 | (±) $CH(CH_3)—CF_3$ | $CH_3$ |
| A-58 | (±) $CH(CH_3)—CF_3$ | $CH_2CH_3$ |
| A-59 | (R) $CH(CH_3)—CF_3$ | H |
| A-60 | (R) $CH(CH_3)—CF_3$ | $CH_3$ |
| A-61 | (R) $CH(CH_3)—CF_3$ | $CH_2CH_3$ |
| A-62 | (S) $CH(CH_3)—CF_3$ | H |
| A-63 | (S) $CH(CH_3)—CF_3$ | $CH_3$ |
| A-64 | (S) $CH(CH_3)—CF_3$ | $CH_2CH_3$ |
| A-65 | (±) $CH(CH_3)—CCl_3$ | H |
| A-66 | (±) $CH(CH_3)—CCl_3$ | $CH_3$ |
| A-67 | (±) $CH(CH_3)—CCl_3$ | $CH_2CH_3$ |
| A-68 | (R) $CH(CH_3)—CCl_3$ | H |
| A-69 | (R) $CH(CH_3)—CCl_3$ | $CH_3$ |
| A-70 | (R) $CH(CH_3)—CCl_3$ | $CH_2CH_3$ |
| A-71 | (S) $CH(CH_3)—CCl_3$ | H |
| A-72 | (S) $CH(CH_3)—CCl_3$ | $CH_3$ |
| A-73 | (S) $CH(CH_3)—CCl_3$ | $CH_2CH_3$ |
| A-74 | $CH_2C(CH_3)=CH_2$ | H |
| A-75 | $CH_2C(CH_3)=CH_2$ | $CH_3$ |
| A-76 | $CH_2C(CH_3)=CH_2$ | $CH_2CH_3$ |
| A-77 | cyclopentyl | H |
| A-78 | cyclopentyl | $CH_3$ |
| A-79 | cyclopentyl | $CH_2CH_3$ |
| A-80 | cyclohexyl | H |
| A-81 | cyclohexyl | $CH_3$ |
| A-82 | cyclohexyl | $CH_2CH_3$ |
| A-83 | —$(CH_2)_4$— | |
| A-84 | (±) —$(CH_2)_2$—$CH(CH_3)$—$CH_2$— | |
| A-85 | (R) —$(CH_2)_2$—$CH(CH_3)$—$CH_2$— | |
| A-86 | (S) —$(CH_2)_2$—$CH(CH_3)$—$CH_2$— | |
| A-87 | —$(CH_2)_2$—$CH(OCH_3)$—$CH_2$— | |
| A-88 | —$(CH_2)_2$—$CH(CH_2CH_3)$—$CH_2$— | |
| A-89 | —$(CH_2)_2$—$CH[CH(CH_3)_2]$—$CH_2$— | |
| A-90 | (±) —$(CH_2)_3$—$CH(CH_3)$— | |
| A-91 | (±) —$CH(CH_3)$—$(CH_2)_2$—$CH(CH_3)$— | |
| A-92 | —$CH_2$—$CH=CH$—$CH_2$— | |
| A-93 | —$(CH_2)_5$— | |
| A-94 | (±) —$(CH_2)_4$—$CH(CH_3)$— | |
| A-95 | —$(CH_2)_2$—$CH(CH_3)$—$(CH_2)_2$— | |
| A-96 | (±) —$(CH_2)_3$—$CH(CH_3)$—$CH_2$— | |
| A-97 | (R) —$(CH_2)_3$—$CH(CH_3)$—$CH_2$— | |
| A-98 | (S) —$(CH_2)_3$—$CH(CH_3)$—$CH_2$— | |
| A-99 | —$(CH_2)_2$—$C(O[CH_2]_2O)$—$(CH_2)_2$— | |
| A-100 |  $(CH_2)_2$—△—$CH_2$ | |

TABLE A-continued

| No. | R¹ | R² |
|---|---|---|
| A-101 | —(CH$_2$)$_2$—C(O[CH$_2$]$_3$O)—(CH$_2$)$_2$— | |
| A-102 | —(CH$_2$)$_2$—CH═CH—CH$_2$— | |

The compounds I are suitable as fungicides. They are distinguished through an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:
  *Alternaria* species on fruit and vegetables,
  *Bipolaris* and *Drechslera* species on cereals, rice and lawns,
  *Blumeria graminis* (powdery mildew) on cereals,
  *Botrytis cinerea* (gray mold) on strawberries, vegetables, ornamental plants and grapevines,
  *Erysiphe cichoracearum* and *Sphaerotheca fuliginea* on cucurbits,
  *Fusarium* and *Verticillium* species on various plants,
  *Mycosphaerella* species on cereals, bananas and peanuts,
  *Phytophthora infestans* on potatoes and tomatoes,
  *Plasmopara viticola* on grapevines,
  *Podosphaera leucotricha* on apples,
  *Pseudocercosporella herpotrichoides* on wheat and barley,
  *Pseudoperonospora* species on hops and cucumbers,
  *Puccinia* species on cereals,
  *Pyricularia oryzae* on rice,
  *Rhizoctonia* species on cotton, rice and lawns,
  *Septoria tritici* and *Stagonospora nodorum* on wheat,
  *Uncinula necator* on grapevines,
  *Ustilago* species on cereals and sugar cane, and
  *Venturia* species (scab) on apples and pears.

The compounds I are also suitable for controlling harmful fungi, such as *Paecilomyces variotii*, in the protection of materials (for example wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted to the customary formulations, for example solutions, emulsions, suspensions, dusts, powders, pastes and granules. The application form depends on the particular intended use; it should in any case ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:
  water, aromatic solvents (for example Solvesso products, xylene), paraffins (for example mineral oil fractions), alcohols (for example methanol, butanol, pentanol, benzyl alcohol), ketones (for example cyclohexanone, gammabutyrolactone), pyrrolidones (NMP, NOP), acetates (glycol diacetate), glycols, fatty acid dimethylamides, fatty acids and fatty acid esters. In principle, solvent mixtures may also be used.
  carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. Products for dilution with water

A) Water-Soluble Concentrates (SL)

10 parts by weight of a compound according to the invention are dissolved in water or in a water-soluble solvent. As an alternative, wetters or other auxiliaries are added. The active compound dissolves upon dilution with water.

B) Dispersible Concentrates (DC)

20 parts by weight of a compound according to the invention are dissolved in cyclohexanone with addition of a dispersant, for example polyvinylpyrrolidone. Dilution with water gives a dispersion.

C) Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D) Emulsions (EW, EO)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturax) and made into a homogeneous emulsion. Dilution with water gives an emulsion.

E) Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F) Water-Dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted

H) Dustable Powders (DP)

5 parts by weight of a compound according to the invention are ground finely and mixed intimately with 95% of finely divided kaolin. This gives a dustable product.

I) Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J) ULV Solutions (UL)

10 parts by weight of a compound according to the invention are dissolved in an organic solvent, for example xylene. This gives a product to be applied undiluted.

The active compounds can be used as such, in the form of their formulations or of the application forms prepared therefrom, e.g. in the form of directly sprayable solutions, powders, suspensions or dispersions, emulsions, oil dispersions, pastes, dusts, preparations for broadcasting or granules, by spraying, atomizing, dusting, broadcasting or watering. The application forms depend entirely on the intended uses; they should always ensure the finest possible dispersion of the active compounds according to the invention.

Aqueous application forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, wetting agents, adjuvants, herbicides, fungicides, other pesticides and bactericides can be added to the active compounds, if appropriate also not until immediately before use (tank mix). These agents can be added to the preparations according to the invention in a weight ratio of 1:10 to 10:1.

The preparations according to the invention can, in the application form as fungicides, also be present together with other active compounds, e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following lists of fungicides, with which the compounds according to the invention can be used in conjunction, is intended to illustrate the possible combinations but does not limit them:

acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidine, such as pyrimethanil, mepanipyrim or cyprodinil, antibiotics, such as cycloheximide, griseofulvin, kasugamycin, natamycin, polyoxin or streptomycin, azoles, such as bitertanol, bromoconazole, cyproconazole, difenoconazole, dinitroconazole, epoxiconazole, fenbuconazole, fluquinconazole, flusilazole, flutriafol, hexaconazole, imazalil, metconazole, myclobutanil, penconazole, propiconazole, prochloraz, prothioconazole, tebuconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrophthalisopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide, strobilurins, such as azoxystrobin, dimoxystrobin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet or tolylfluanid, cinnamides and analogous compounds, such as dimethomorph, flumetover or flumorph.

SYNTHESIS EXAMPLES

Example 1

Synthesis of 1-[4-chloro-6-(2,2,2-trifluoro-1-methylethylamino)-5-(2,4,6-trifluorophenyl)pyrimidin-2-yl]-pyrrolidin-2-one [I-2]

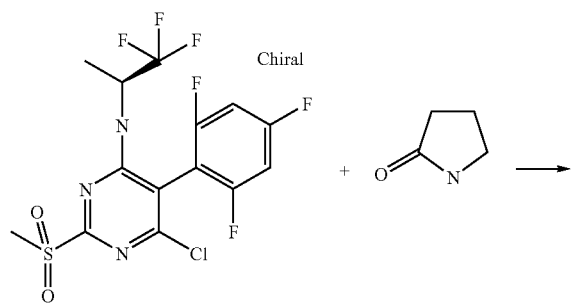

-continued

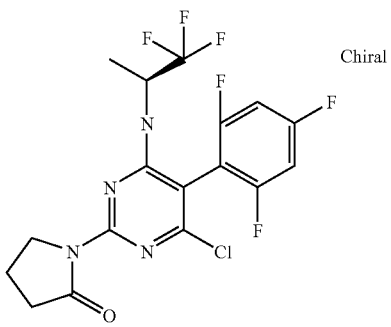

The synthesis was carried out analogously to MCALONAN, H.; MONTGOMERY, D.; STEVENSON, P. J.; Tetrahedron Lett. 1996, 37 (39), 7151-7154.

206 mg (2.4207 mmol) of 2-pyrrolidinone in 5 ml THF p.a. were cooled to −78° C., at −78° C., 2.7665 mmol of a 2M LDA solution in THF/n-hexane were added dropwise and the mixture was stirred for 15 min. 1000 mg (2.3054 mmol) of the abovementioned sulfone, dissolved in 5 ml THF p.a., were then added dropwise, the dry-ice bath was removed and the mixture was stirred at room temperature overnight.

Distilled water was added, the mixture was extracted with methyl tert-butyl ether and the organic phase was dried over $MgSO_4$ and concentrated using a rotary evaporator. This gave a slightly beige solid in a yield of 65%.

MSD: product mass M=439(+H);

m.p.: 142-145° C.

Example 2

Synthesis of 1-[4-chloro-6-(2,2,2-trifluoro-1-methylethylamino)-5-(2-chloro-6-fluorophenyl)pyrimidin-2-yl]pyridazolidin-3-one [I-7]

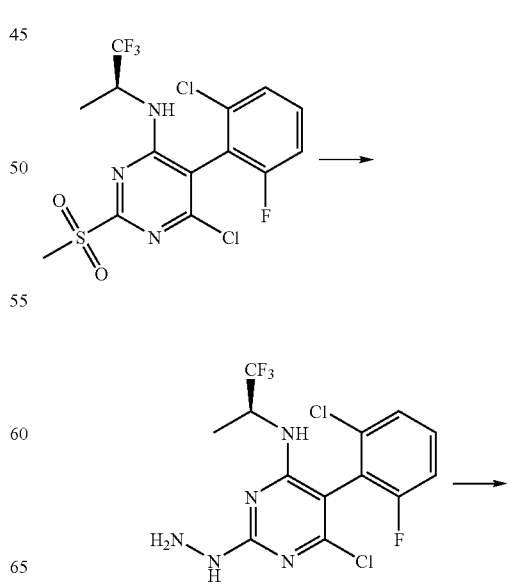

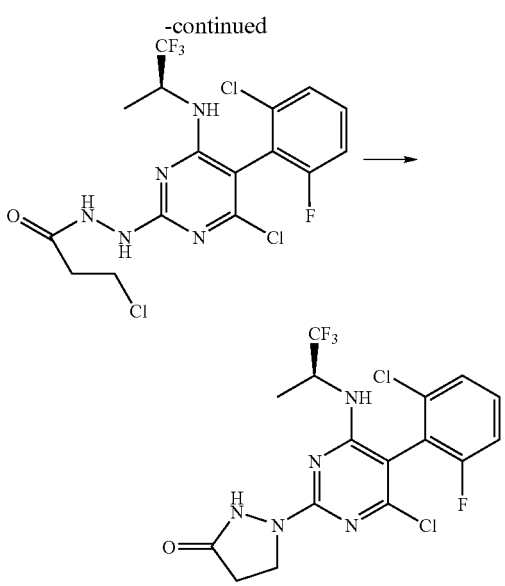

2.1) [4-Chloro-2-hydrazino-5-(2-chloro-6-fluorophenyl)pyrimidin-6-yl]-(2,2,2-trifluoro-1-methylethyl)amine 18.1 g (0.042 mol) of the sulfone [4-chloro-2-methylsulfenyl-5-(2-chloro-6-fluorophenyl)pyrimidin-6-yl]-(2,2,2-trifluoro-1-methylethyl)amine were initially charged in 100 ml of ethanol, and 4.7 g (0.093 mol) of hydrazine hydrate were added dropwise to this mixture. The mixture was stirred at room temperature overnight. The mixture was concentrated and the residue was dissolved in ethyl acetate, washed with water, dried over magnesium sulfate and concentrated. The residue was triturated with diisopropyl ether and the crystals were filtered off with suction, washed with diisopropyl ether and n-pentane and dried under reduced pressure. This gave 10.8 g (67% yield) of a solid of melting point 120-122° C.

2.2) N'-[4-Chloro-6-(2,2,2-trifluoro-1-methylethylamino)-5-(2-chloro-6-fluorophenyl)pyrimidin-2-yl]-3-chloropropionohydrazide 0.60 g (1.6 mmol) of the compound synthezised in 2.1 were dissolved in 10 ml of absolute methylene chloride, and 0.20 g (2.4 mmol) of pyridine were added. At 0-10° C., 0.25 g (1.9 mmol) of 3-chloropropionyl chloride in 1 ml of absolute methylene chloride were then added dropwise. The mixture was stirred at room temperature overnight, diluted with methylene chloride and washed successively with saturated sodium bicarbonate solution, 5% strength acetic acid and water, dried over magnesium sulfate and concentrated. The residue was purified by flash chromatography on silica gel using methyl tert-butyl ether/hexane. This gave 0.5 g (66% yield) of a colorless solid of melting point 152-156° C.

2.3) Synthesis of 1-[4-chloro-6-(2,2,2-trifluoro-1-methylethylamino)-5-(2-chloro-6-fluorophenyl)pyrimidin-2-yl]pyridazolidin-3-one Under protective gas, 130 mg (1.3 mmol) of diisopropylamine and 5 ml of absolute THF were initially charged, and 0.8 ml (1.3 mmol) of a 1.6 molar solution of butyllithium in hexane were added dropwise at −78° C. The mixture was stirred at −78° C. for 30 minutes and then added dropwise to a solution of 0.3 g (0.63 mmol) of the amide 2.2 in 5 ml of absolute THF. The mixture was warmed to room temperature over a period of 3-4 hours and then stirred at room temperature overnight. Water was added, the mixture was extracted with methyl tert-butyl ether, washed with water and the extract was dried over magnesium sulfate and concentrated. Purification by preparative HPLC gave 50 mg of a yellow solid (18% yield) of melting point 214-217° C.

With appropriate modification of the starting materials, the procedures given in the synthesis examples above were used to obtain further compounds I. The compounds obtained in this manner are listed in Table I below, together with physical data.

TABLE I

| No. | HET | $R^1$ | $R^2$ | $L_n$ | m.p. [° C.] |
|---|---|---|---|---|---|
| I-1 | pyrrolidin-2-one-1-yl | —CH$_2$CH=CH$_2$ | —(CH$_2$)$_2$CH$_3$ | 2-chloro-4-fluoro | 124-127 |
| I-2 | pyrrolidin-2-one-1-yl | (S) —CH(CH$_3$)CF$_3$ | H | 2,4,6-trifluoro | 141-145 |

TABLE I-continued
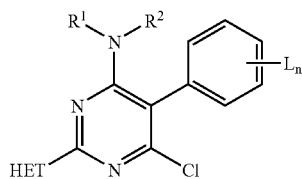
| No. | HET | R¹ | R² | L_n | m.p. [° C.] |
|---|---|---|---|---|---|
| I-4 | 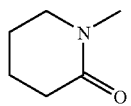 | (S) —CH(CH₃)CF₃ | H | 2,4,6-trifluoro | 122-127 |
| I-5 | 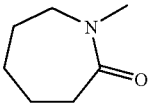 | (S) —CH(CH₃)CF₃ | H | 2,4,6-trifluoro | 168-170 |
| I-6 | 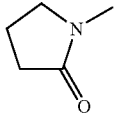 | —CH₂CF₃ | H | 2,4,6-trifluoro | 192-193 |
| I-7 | 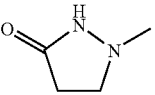 | (S) —CH(CH₃)CF₃ | H | 2-chloro-6-fluoro | 214-217 |
| I-8 | 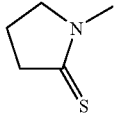 | (S) —CH(CH₃)CF₃ | H | 2,4,6-trifluoro | 86-94 |
| I-9 | 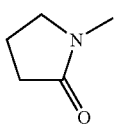 | (R) —CH(CH₃)CF₃ | H | 2,4,6-trifluoro | 142-145 |
| I-10 | 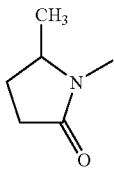 | (S) —CH(CH₃)CF₃ | H | 2,4,6-trifluoro | 65-81 |
| I-11 | 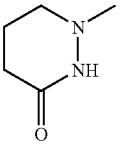 | (S) —CH(CH₃)CF₃ | H | 2-chloro-6-fluoro | 1H-NMR: δ (ppm, CDCl₃) = 1.3 (s, 3H); 2.15 (m, 2H); 2.5 (m, 2H); 3.75 (m, 2H); 4.3 (m, 1H); 4.92 (m, 1H); 7.18 (m, 1H); 7.4 (m, 2H) |

TABLE I-continued
| No. | HET | R¹ | R² | L$_n$ | m.p. [° C.] |
|---|---|---|---|---|---|
| I-12 | 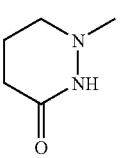 | —CH(CH₃)C₂H₅ | H | 2-chloro-6-fluoro | H-NMR: δ (ppm, CDCl₃) = 0.83 (m, 3H); 1.12 (m, 3H); 1.45 (m, 2H); 2.15 (m, 2H); 2.48 (m, 2H); 3.75 (m, 2H); 4.2 (s, 1H); 4.33 (m, 1H); 7.15(m, 1H); 7.4 (m, 2H) |
| I-13 | 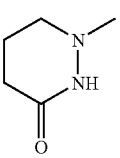 | —(CH₂)₂—CH(CH₃)—(CH₂)₂— | | 2-chloro-6-fluoro | H-NMR: δ (ppm, CDCl₃) = 0.88 (d, 3H); 1.0 (q, 2H); 1.45 (s, 1H); 1.49 (s, 2H); 2.13 (m, 2H); 2.48 (t, 2H); 2.68 (t, 2H); 3.75 (t, 2H); 3.85 (t, 2H); 7.08 (t, 1H); 7.3 (m, 2H) |
| I-14 | 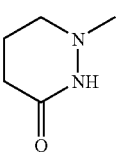 | —CH(CH₃)C₂H₃ | H | 2,4,6-trifluoro | 1H-NMR: δ (ppm, CDCl₃) = 0.85 (t, 3H); 1.1 (d, 3); 1.45 (m, 2H); 2.15 (m, 2H); 2.47 (t, 2H); 3.75 (t, 2H); 4.0 (m, 1H); 4.2 (m, 1H); 6.8 (t, 2H) |
| I-15 | 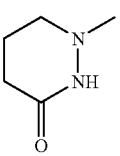 | —(CH₂)₂—CH(CH₃)—(CH₂)₂— | | 2,4,6-trifluoro | 1H-NMR: δ (ppm, CDCl₃) = 0.88 (m, 3H), 1.0 (q, 2H); 1.5 (s, 1H); 1.52 (s, 2H); 2.15 (m, 2H);; 2.48 (t, 2H); 2.72 (m, 2H); 2.72 (t, 2H); 3.85 (d, 2H); 6.75 (m, 2H) |

TABLE I-continued

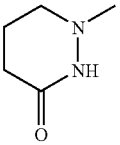

| No. | HET | R¹ | R² | Lₙ | m.p. [° C.] |
|-----|-----|-----|-----|-----|-----|
| I-16 | 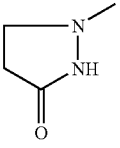 | (S)—CH(CH₃)CF₃ | H | 2,4,6-trifluoro | 1H-NMR: δ (ppm, CDCl₃) = 1.3 (d, 3H); 2.16 (m, 2H); 2.5 (m, 2H); 3.72 (m, 2H); 4.35 (m, 1H); 4.9 (m, 1H); 6.85 (m, 2H) |
| I-17 | 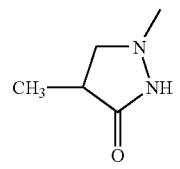 | (S)—CH(CH₃)CF₃ | H | 2,4,6-trifluoro | 1H-NMR: δ (ppm, acetone) = 1.5 (d, 3H); 2.75 (m, 2H); 4.2 (t, 2H); 5.6 (m, 1H); 6.62 (d, 1H); 7.08 (m, 2H) |
| I-18 | 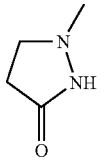 | (S)—CH(CH₃)CF₃ | H | 2,4,6-trifluoro | 200 |
| I-19 | 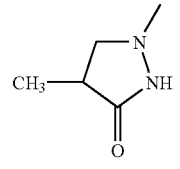 | (S)—CH(CH₃)C₂H₅ | H | 2-chloro-6-fluoro | 1H-NMR: δ (ppm, CDCl₃) = 0.85 (m, 3H); 1.1 (m, 3H); 1.45 (m, 2H); 2.8 (t, 2H); 4.12 (s, 2H); 4.25 (t, 2H); 7.15 (m, 1H); 7.38 (m, 2H |
| I-20 | | (S)—CH(CH₃)CF₃ | H | 2-chloro-6-fluoro | 195-198 |

The parent pyrimidine bears $R^1R^2N$-, HET, Cl, and an aryl group with $L_n$ substituents.

TABLE I-continued

| No. | HET | R¹ | R² | L$_n$ | m.p. [° C.] |
|---|---|---|---|---|---|
| I-21 | 1-methyl-4-methyl-pyrazolidin-3-one | —CH(CH₃)C₂H₅ | H | 2-chloro-6-fluoro | 1H-NMR: δ (ppm, CDCl₃) = 0.86 (m, 3H); 1.11 (t, 3H); 1.36 (d, 3H); 1.45 (m, 2H); 2.97 (m, 1H); 3.65 (t, 1H); 4.1 (s, 2H); 4.55 (t, 1H); 7.15 (t, 1H); 7.39 (m, 2H) |
| I-22 | 1-methyl-pyrazolidin-3-one | —(CH₂)₂—CH(CH₃)—(CH₂)₂— | | 2-chloro-6-fluoro | 142-145 |
| I-23 | 1-methyl-4-methyl-pyrazolidin-3-one | —(CH₂)₂—CH(CH₃)—(CH₂)₂— | | 2-chloro-6-fluoro | 180-183 |
| I-24 | 1-methyl-pyrazolidin-3-one | —CH(CH₃)C₂H₅ | H | 2,4,6-trifluoro | 205-208 |
| I-25 | 1-methyl-4-methyl-pyrazolidin-3-one | —CH(CH₃)C₂H₅ | H | 2,4,6-trifluoro | 193-196 |
| I-26 | 1-methyl-pyrazolidin-3-one | —(CH₂)₂—CH(CH₃)—(CH₂)₂— | | 2,4,6-trifluoro | 1H-NMR: δ (ppm, CDCl₃) = 0.9 (d, 3H); 1.0 (q, 2H); 1.5 (s, 1H); 1.52 (s, 2H); 2.7 (t, 2H); 2.8 (t, 2H); 3.85 (d, 2H); 4.2 (t, 2H); 6.75 (m, 2H) |

TABLE I-continued

| No. | HET | R¹ | R² | $L_n$ | m.p. [° C.] |
|---|---|---|---|---|---|
| I-27 | (structure with CH₃, N, NH, O) | | —(CH₂)₂—CH(CH₃)—(CH₂)₂— | 2,4,6-trifluoro | 185-188 |

Examples of the Action Against Harmful Fungi

The fungicidal action of the compounds of the formula I was demonstrated by the following experiments:

The active compounds were prepared separately as a stock solution with 0.25% by weight of active compound in acetone or DMSO. 1% by weight of the emulsifier Uniperol® EL (wetting agent having emulsifying and dispersing action based on ethoxylated alkylphenols) was added to this solution. The stock solution of the active compounds were diluted with water to the desired concentration.

USE EXAMPLES

1. Activity Against Gray Mold on Bell Pepper Leaves Caused by *Botrytis cinerea*, Protective Application Bell pepper seedlings of the cultivar "Neusiedler Ideal Elite" were, after 4-5 leaves were well developed, sprayed to runoff point with an aqueous suspension having an active compound concentration of 250 ppm. The next day, the treated plants were inoculated with a spore suspension of *Botrytis cinerea* which contained 1.7×10⁶ spores/ml in a 2% strength aqueous biomalt solution. The test plants were then placed in a climatized chamber at 22 to 24° C. and high atmospheric humidity. After 5 days, the extent of the fungal infection on the leaves could be determined visually in %.

In this test, the plants which had been treated with compounds I-2, I-4, I-6, I-7, I-9, I-11, I-17, I-18, I-19, I-20, I-21, I-22, I-24 and I-25 were less than 5% infected, whereas the untreated plants were 90% infected.

2. Activity Against Early Blight of Tomato Caused by *Alternaria solani*

Leaves of potted plants of the cultivar "Golden Princess" were sprayed to runoff point with an aqueous suspension of the active compound concentration given below. The next day, the leaves were infected with an aqueous spore suspension of *Alternaria solani* in 2% biomalt solution with a concentration of 0.17×10⁶ spores/ml. The plants were then placed in a water-vapor-saturated chamber at temperatures between 20 and 22° C. After 5 days, the early blight on the untreated but infected control plants had developed to such an extent that the infection could be determined visually in %.

In this test, the plants which had been treated with compounds I-2, I-4, I-6 and I-7 were less than 10% infected, whereas the untreated plants were 90% infected.

3. Activity Against Net Blotch of Barley Caused by *Pyrenophora teres*, 1 Day Protective Application Leaves of potted barley seedlings were sprayed to runoff point with an aqueous suspension having the active compound concentration stated below. 24 hours after the spray coating had dried on, the test plants were inoculated with an aqueous spore suspension of *Pyrenophora* [syn. *Drechslera*] *teres*, the net blotch pathogen. The test plants were then placed in a greenhouse at temperatures between 20 and 24° C. and 95 to 100% relative atmospheric humidity. After 6 days, the extent of the development of the disease was determined visually in % infection of the entire leaf area.

In this test, the plants which had been treated with compounds I-11, I-17, I-18, I-19, I-20, I-21, I-22, I-24 and I-25 were less than 20% infected, whereas the untreated plants were 90% infected.

We claim:

1. A 2-substituted pyrimidine of the formula I

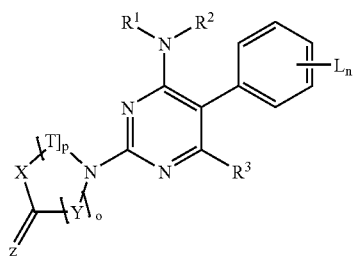

in which the indices and the substituents are as defined below:
n is an integer from 1 to 5;
L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, —C(=O)—N(A')A, C(A')(=N—OA), N(A')A, N(A')—C(=O)-A, N(A")—C(=O)—N(A')A, S(=O)$_m$-A, S(=O)$_m$—O-A or S(=O)$_m$—N(A')A,
m is 0, 1 or 2;
A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated heterocyclic group or a five membered saturated, partially unsaturated or heterocyclic aromatic ring or aromatic heterocycle which comprises one to four heteroatoms from the group consisting of O, N and S;

where the aliphatic groups of the radical definitions of L for their part may be partially or fully halogenated or may carry one to four groups $R^u$:

$R^u$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy —C(=O)-A, —C(=O)—O-A, —C(=O)—N(A')A, C(A')(=N—OA), N(A')A, N(A')—C(=O)-A, N(A")-C(=O)—N(A')A, S(=O)$_m$-A, S(=O)$_m$—O-A or S(=O)$_m$—N(A')A;

$R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")—C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether -(—O—), carbonyl —(C=O)—, thio -(—S—), sulfoxyl -(—S[=O]—) or sulfonyl -(—SO$_2$—) group or by a further amino -(—N($R^a$)— group, where $R^a$ is hydrogen or $C_1$-$C_6$-alkyl, and/or may be bonded to one or more substituents from the group consisting of halogen, $C_1$-$C_6$-alkyl, and $C_1$-$C_6$-haloalkyl;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

X is a group —CH—$R^a$—, —N—$R^b$—, —O— or —S—;

$R^a$ may be hydrogen, halogen, $C_1$-$C_6$-alkyl, $C_1$-$C_6$-alkoxy, cyano or $C_1$-$C_6$-alkoxycarbonyl;

$R^b$ is hydrogen, $C_1$-$C_6$-alkyl or $C_3$-$C_6$-cycloalkyl;

T is a group —CH—$R^a$—;

p is an integer from 1 to 4;

Y is a group —CH—$R^a$— or —N—$R^b$—, o is 0 or 1;

Z is O, S or a group N($R^c$)

$R^c$ is hydrogen, $C_1$-$C_6$-alkyl or $C_1$-$C_6$-alkoxy.

2. The 2-substituted pyrimidine of the formula I according to claim 1 where n is an integer from 1 to 3, where at least one substituent L is located in the ortho-position on the phenyl ring;

L is halogen, cyano, methyl, methoxy, —C(=O)—O-A, —C(=O)—N(A')A, C(A')(=N—OA), N(A')A, N(A')—C(=O)-A, A,A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A' together with the atoms to which they are attached are a five- or six-membered saturated heterocycle which comprises one or two heteroatoms from the group consisting of O, N and S;

where the aliphatic groups of the radical definitions of L for their part may be partially or fully halogenated;

$R^1$,$R^2$ independently of one another are $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or $C_2$-$C_6$-haloalkynyl;

$R^2$ may additionally be hydrogen;

$R^1$ and $R^2$ may also, together with the nitrogen atom to which they are attached, form a saturated or unsaturated five- or six-membered ring which may be interrupted by an ether -(—O—) or by a further amino -(—N($R^a$)— group, where $R^a$ is hydrogen or $C_1$-$C_6$-alkyl, and/or may be bonded to one or more substituents from the group consisting of halogen, $C_1$-$C_6$-alkyl, and $C_1$-$C_6$-haloalkyl;

$R^3$ is halogen, cyano, $C_1$-$C_4$-alkoxy or $C_1$-$C_4$-haloalkyl;

X is a group —CH—$R^a$—;

$R^a$ is hydrogen or $C_1$-$C_3$-alkyl, p is an integer from 2 to 4 and o is 0.

3. The 2-substituted pyrimidine according to claim 1 where $R^3$ is chlorine, cyano, methyl or methoxy.

4. The 2-substituted pyrimidine according to claim 1 where

X is a group —CH—$R^a$—;

$R^a$ is hydrogen, halogen, cyano or $C_1$-$C_3$-alkyl;

T is a group —CH—$R^a$—;

p is an integer from 1 to 3;

Y is a group —N—$R^b$ $R^b$ is hydrogen or $C_1$-$C_3$-alkyl and o is 1.

5. The 2-substituted pyrimidine according to any of claims 1 to 4 in which the phenyl group substituted by $L_n$ is the group B where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, nitro, $CH_3$, $SCH_3$, $OCH_3$, $SO_2CH_3$, $NH-C(=O)CH_3$, $N(CH_3)-C(=O)CH_3$ or $COOCH_3$ and $L^5$ is hydrogen, fluorine, chlorine or $CH_3$.

6. A process for preparing the compounds IA by reacting the sulfone II with the nucleophile III, where the index p is 2 to 5, under basic conditions to give the lactam IA

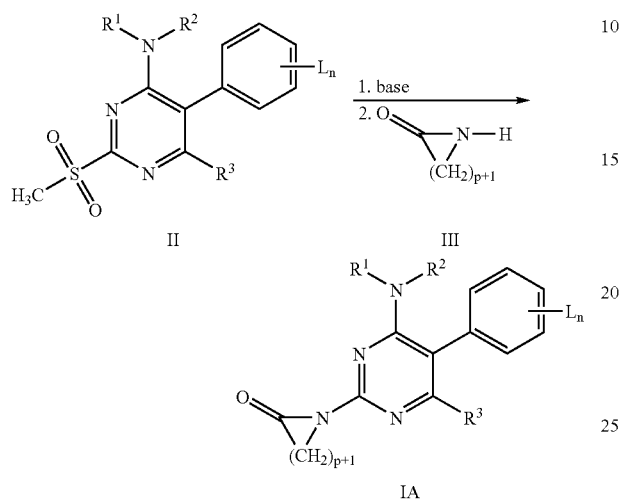

wherein $R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, $-C(=O)$-A, $-C(=O)-$ O-A, $-C(=O)-N(A')A$, $C(A')(=N-OA)$, $N(A')$ A, $N(A')-C(=O)$-A, $N(A")-C(=O)-N(A')A$, $S(=O)_m$-A, $S(=O)_m$-O-A or $S(=O)_m-N(A')A$ or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, $-C(=O)$-A, $-C(=O)-$O-A, $-C(=O)-N(A')A$, $C(A')(=N-OA)$, $N(A')A$;

$R^2$ may additionally be hydrogen;

$R^1$ and $R^2$ may also, together with the nitrogen atom to which they are attached, form a saturated or unsaturated five- or six-membered ring which may be interrupted by an ether -($-O-$), carbonyl $-(C=O)-$, thio -($-S-$), sulfoxyl -($-S[=O]-$) or sulfonyl -($-SO_2-$) group or by a further amino -($-N(R^a)-$ group, where $R^a$ is hydrogen or $C_1$-$C_6$-alkyl, and/or may be bonded to one or more substituents from the group consisting of halogen, $C_1$-$C_6$-alkyl, and $C_1$-$C_6$-haloalkyl;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl.

7. A process for preparing the compounds IB by reacting the hydrazine IV with a chloroalkylcarbonyl chloride, where the index p is 2 or 3, to give the compound V and subsequent cyclization to give the pyrazolone IB

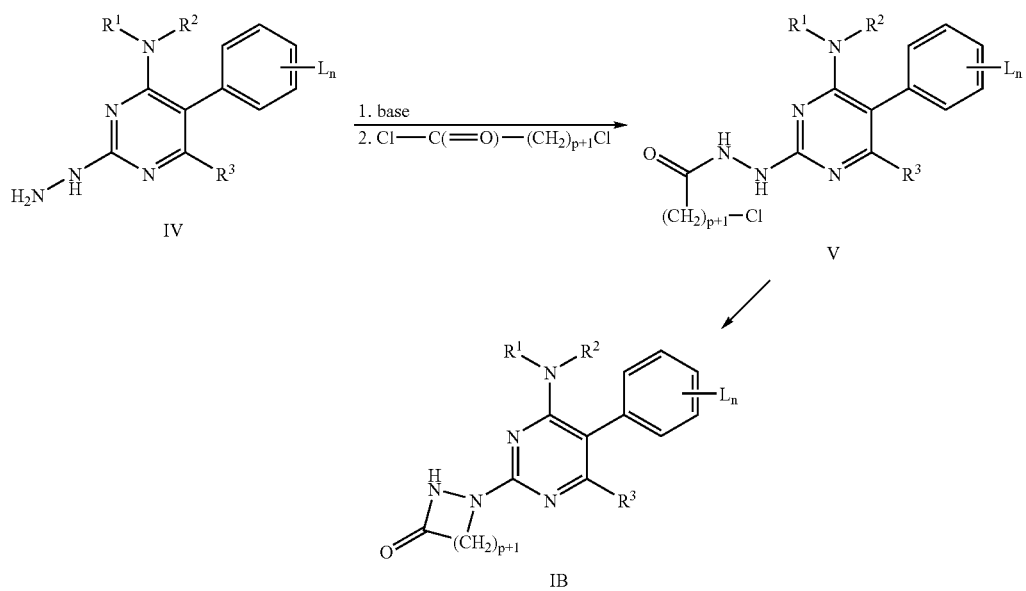

wherein $R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, $-C(=O)$-A, $-C(=O)-$ O-A, —C(=O)—N(A')A, C(A')(=N—OA), N(A')A, N(A')—C(=O)-A, N(A")-C(=O)—N(A')A, S(=O)-A, S(=O)—O-A or $S(=O)_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether -(—O—), carbonyl —(C=O)—, thio -(—S—), sulfoxyl -(—S[=O]—) or sulfonyl -(—$SO_2$—) group or by a further amino -(—N($R^a$)— group, where $R^a$ is hydrogen or $C_1$-$C_6$-alkyl, and/or may be bonded to one or more substituents from the group consisting of halogen, $C_1$-$C_6$-alkyl, and $C_1$-$C_6$-haloalkyl;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl.

8. A pesticidal composition which comprises a solid or liquid carrier and a compound of the formula I according to claim 1.

9. A method for controlling phytopathogenic harmful fungi which comprises treating the fungi or the materials, plants, the soil or the seeds to be protected against fungal attack with an effective amount of a compound of the formula I according to claim 1.

* * * * *